United States Patent [19]

Biller

[11] Patent Number: 5,166,386
[45] Date of Patent: Nov. 24, 1992

[54] PROCESS OF MAKING ISOPRENOID PHOSPHINYLFORMIC ACID SQUALENE SYNTHETASE INHIBITORS

[75] Inventor: Scott A. Biller, Ewing, N.J.

[73] Assignee: E. R. Squibb & Sons, Inc., Princeton, N.J.

[21] Appl. No.: 811,130

[22] Filed: Dec. 20, 1991

Related U.S. Application Data

[62] Division of Ser. No. 650,823, Feb. 5, 1991, Pat. No. 5,107,011, which is a division of Ser. No. 408,974, Sep. 18, 1989, Pat. No. 5,025,003.

[51] Int. Cl.$^5$ .......................... C07F 9/30; C07F 9/32
[52] U.S. Cl. .................................. 558/124; 558/137; 558/181
[58] Field of Search ............................... 558/181, 124

[56] References Cited

U.S. PATENT DOCUMENTS

| 3,943,201 | 3/1976 | McIntosh | 558/181 |
| 4,018,854 | 4/1977 | McIntosh | 558/181 |
| 4,386,081 | 5/1983 | Helgstrand et al. | 558/181 X |

FOREIGN PATENT DOCUMENTS

1294809  3/1987  U.S.S.R. .............................. 558/181

OTHER PUBLICATIONS

Issleib, K. et al., *Synth. React. Inorg. Met.-Org. Chem.* 1986, 16(9), 1253-; *Chem. Abstr.* 1988, 108, 37928h.

Kosolapoff, G. M. et al., *Organic Phosphorus Compounds;* vol. 4; Wiley–Interscience: New York, 1972; pp. 266–267.

Poulter, C. D., et al.,*Biosynthesis of Isoprenoid Compounds,* "Conversion of Farnesyl Pyrophosphate to Squalene", vol. 1, Chapter 8, pp. 413–441, J. Wiley and Sons, 1981.

Faust, J. R., et al., *Proc. Nat. Acad. Sci., USA*, "Squalene synthetase activity in human fibroblasts: Regulation via the low density lipoprotein receptor", 1979, 76, 5018–5022.

de Montellano, P. Ortiz, et al., *J. Med. Chem.*, "Inhibition of Squalene Synthetase by Farnesyl Pyrophosphate Analogues", 1977, 20, 243–249.

Corey and Volante, *J. Am. Chem. Soc.*, "Application of Unreactive Analogs of Terpenoid Pyrophosphates to Studies of Multistep Biosynthesis, Demonstration that 'Presqualene Pyrophosphate', is an Essential Intermediate on the Path to Squalene", 1976, 98, 1291–3.

Sandifer, R. M. et al., *J. Am. Chem. Soc.*, 1982, 104, 7376–8, "Squalene Synthetase, Inhibition, by an Ammonium Analogue of a Carbocationic Intermediate in the Conversion of Presqualene Pyrophosphate to Squalene".

Bertolino, A., et al., *Biochim. Biophys. Acta.*, 1978, 530, 17–23, "Polyisoprenoid Amphiphilic Compounds as Inhibitors of Squalene Synthesis and Other Microsomal Enzymes".

Davisson, F. J., et al., *J. Org. Chem.*, 1986, 51, 4766–4779, "Phosphorylation of Isoprenoid Alcohols".

Stremler, K. E. et al., *J.A.C.S.*, 1987, 109, 5542, "Methane and Difluoromethanediphosphonate Analogues of Geranyl Diphosphate: Hydrolysis-Inert Alternate Substrates".

McClard, R. W., et al., *J. Am. Chem. Soc.*, 1987, 109, 5544–5545, "Novel Phosphonylphosphinyl (P–C–P–C) Analogues of Biochemically Interesting Diphosphates, Syntheses and Properties of P–C–P–C Analogues of Isopentenyl Diphosphate and Dimethylallyl Diphosphate".

Capson, T. L., PhD dissertation, Jun. 1987, Dept. of Medicinal Chemistry, the University of Utah, Abstract, Table of Contents, pp. 16, 17, 40–43, 48–51, Summary.

Biller, S. A., et al., *J. Med. Chem.*, 1988, 31, 1869 "Isoprenoid(Phosphinylmethyl)phosphonates as Inhibitors of Squalene Synthetase".

Merck Index, Tenth Edition, p. 607, paragraph 4135, (1983).

Kosolapoff, G. M., "Organophosphorus Compounds", John Wiley and Sons, 1950, pp.146–147.

*Primary Examiner*—Mary C. Lee
*Assistant Examiner*—Michael G. Ambrose
*Attorney, Agent, or Firm*—Burton Rodney

[57] ABSTRACT

Compounds which are inhibitors of cholesterol biosynthesis (by inhibiting de novo squalene biosynthesis), and thus are useful as hypocholesterolemic agents and antiatherosclerotic agents, are provided which have the structure

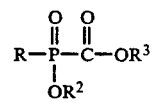

wherein $R^2$ is a metal ion, lower alkyl or H;
$R^3$ is a metal ion or lower alkyl;
R is $R^1$—$(CH_2)_n$—, $R^1$—$(CH_2)_m$—O— or
$R^1$—$(CH_2)_m$—$OCH_2$—, wherein n is 1 to 4 and m is 0 to 3, and
$R^1$ is $R^5$—$Q^1$—$Q^2$—$Q^3$—wherein $R^5$, $Q^1$, $Q^2$ and $Q^3$ are as defined herein.

New intermediates, new methods of preparation and a method for using such compounds to inhibit cholesterol biosynthesis are also provided.

7 Claims, No Drawings

PROCESS OF MAKING ISOPRENOID PHOSPHINYLFORMIC ACID SQUALENE SYNTHETASE INHIBITORS

This is a division of application Ser. No. 650,823, filed Feb. 5, 1991 now U.S. Pat. No. 5,107,0, which is a division of application Ser. No. 408,974, filed Sept. 18, 1989 now U.S. Pat. No. 5,025,003.

FIELD OF THE INVENTION

The present invention relates to new isoprenoid phosphinylformic acid compounds which are useful in inhibiting cholesterol biosynthesis by inhibiting de novo squalene production, to hypocholesterolemic and antiatherosclerotic compositions containing such compounds and to a method of using such compounds for inhibiting cholesterol biosynthesis and atherosclerosis.

BACKGROUND OF THE INVENTION

Squalene synthetase is a microsomal enzyme which catalyzes the reductive dimerization of two molecules of farnesyl pyrophosphate (FPP) in the presence of nicotinamide adenine dinucleotide phosphate (reduced form) (NADPH) to form squalene (Poulter, C. D.; Rilling, H. C., in "Biosynthesis of Isoprenoid Compounds", Vol. I, Chapter 8, pp. 413–441, J. Wiley and Sons, 1981 and references therein). This enzyme is the first committed step of the de novo cholesterol biosynthetic pathway. The selective inhibition of this step should allow the essential pathways to isopentenyl tRNA, ubiquinone, and dolichol to proceed unimpeded. Squalene synthetase, along with HMG-CoA reductase has been shown to be down-regulated by receptor mediated LDL uptake (Faust, J. R.; Goldstein, J. L.; Brown, M. S. *Proc. Nat. Acad. Sci. USA*, 1979, 76, 5018–5022), lending credence to the proposal that inhibiting squalene synthetase will lead to an up-regulation of LDL receptor levels, as has been demonstrated for HMG-CoA reductase, and thus ultimately should be useful for the treatment and prevention of hypercholesterolemia and atherosclerosis.

One approach to inhibitors of squalene synthetase is to design analogs of the substrate FPP. It is clear from the literature that the pyrophosphate moiety is essential for binding to the enzyme. However, such pyrophosphates are unsuitable as components of pharmacological agents due to their chemical and enzymatic lability towards allylic C-0 cleavage, as well as their susceptibility to metabolism by phosphatases.

P. Ortiz de Montellano et al in *J. Med. Chem.*, 1977, 20, 243–249 describe the preparation of a series of substituted terpenoid pyrophosphate (Table A), and have shown these to be competitive inhibitors of the squalene synthetase enzyme. These substances retain the unstable allylic pyrophosphate moiety of FPP.

TABLE A

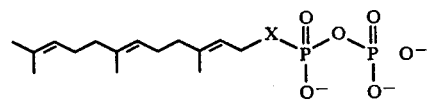

| No. | X | Y | Z |
|---|---|---|---|
| 1 | CH₃ | CH₃ | H |
| 2 | H | H | H |
| 3 | C₂H₅ | H | H |
| 4 | I | H | H |
| 5 | H | I | H |

TABLE A-continued

| No. | X | Y | Z |
|---|---|---|---|
| 6 | CH₃ | H | SCH₃ |

Corey and Volante, *J. Am. Chem. Soc.* 1976, 98, 1291-3, have prepared FPP analog A and presqualene pyrophosphate (PSQ-PP) analog B as inhibitors of squalene biosynthesis. (Presqualene pyrophosphate is an intermediate in the conversion of FPP to squalene). These inhibitors possess methylene groups in place of the allylic oxygen moiety of FPP and PSQ-PP, but still retain the chemically and enzymatically unstable pyrophosphate linkage.

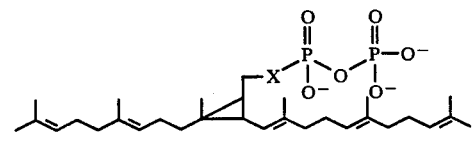

A  X = CH₂
FPP X = O

B    X = CH₂
PSQ—PP X = O

Poulter and co-workers have prepared cyclopropane C (Sandifer, R. M., et al., *J. Am. Chem. Soc.* 1982, 104, 7376-8) which in the presence of inorganic pyrophosphate is an intermediate analog inhibitor of the enzyme squalene synthetase.

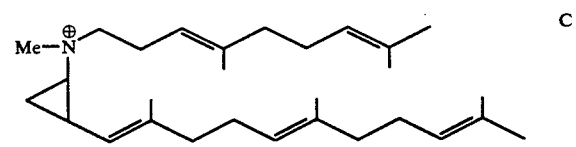

Altman and co-workers, Bertolino, A., et al., *Biochim. Biophys. Acta.* 1978, 530, 17–23, reported that farnesyl amine and related derivatives D inhibit squalene synthetase, but provide evidence that this inhibition is non-specific and probably related to membrane disruption.

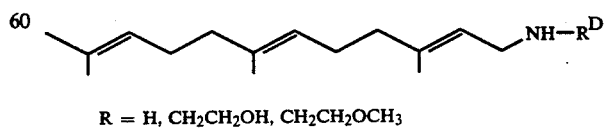

R = H, CH₂CH₂OH, CH₂CH₂OCH₃

Poulter, C.D., et al, *J. Org. Chem.*, 1986, 51, 4768, prepared compound E in a demonstration of a synthetic method, but did not report any biological data.

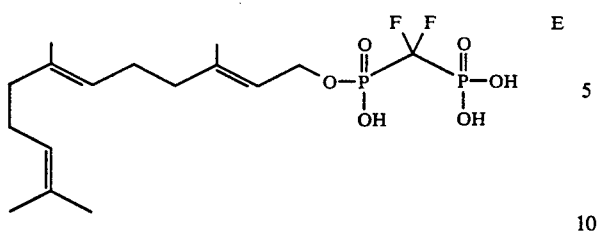

E

Poulter, C. D., Stremler, K. E., *J.A.C.S.*, 1987, 109, 5542 describes the synthesis and biological evaluation of compounds having structure F. These compounds were evaluated as alternative substrates for avian liver and lemon peel farnesyl diphosphate cyclase.

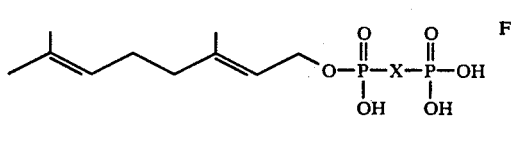

F $X = CH_2, CF_2$

McClard, R. W. and Poulter, C. D., et al., *J.A.C.S.* 1987, 109, 5544, reported that phosphinylphosphonates G and H were competitive inhibitors of the 1'-4-condensation between isopentenyl diphosphate and geranyl diphosphate catalyzed by avian liver farnesyl diphosphate synthetase. Phosphinylphosphonates G and H had Ki's of 19μM and 71μM, respectively. They also reported the speculative isolation of the farnesyl phosphinylphosphonate I, and the geranyl phosphinylphosphonate J from the enzymatic reaction of G with geranyl pyrophosphate or dimethylallyl pyrophosphate, respectively. The structures of I and J were tentatively assigned based on relative TLC mobilities. They hypothesized that I could be a potential inhibitor of squalene synthetase.

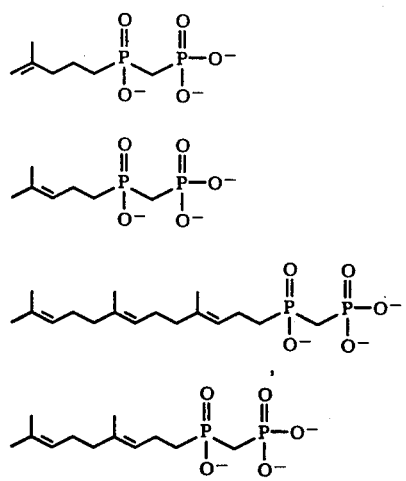

G

H

I

J

Capson, T. L., PhD dissertation, June 1987, Dept. of Medicinal Chemistry, the University of Utah, Abstract, Table of Contents, pp. 16, 17, 40–43, 48–51, Summary, and T. L. Capson, C. D. Poulter et al, *J. Org. Chem.*, 1988, 53, 5903–5908 disclose cyclopropanes of the structure K

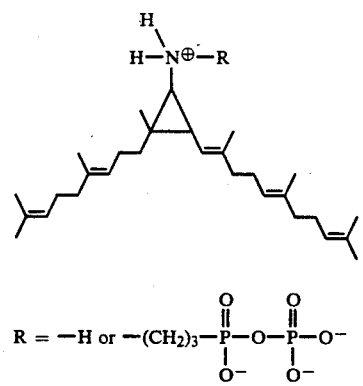

K $$R = -H \text{ or } -(CH_2)_3-\overset{O}{\underset{O^-}{P}}-O-\overset{O}{\underset{O^-}{P}}-O^-$$

as intermediate analog inhibitors of squalene synthetase.

Biller and coworkers, "Isoprenoid (Phosphinylmethyl)phosphonates as Inhibitors of Squalene Synthetase," J. Med. Chem., 1988, 31, 1869, synthesized analogues of FPP, 2a-d and 3a,b, where the allylic and anhydride oxygen atoms are replaced with carbon. The PMP subunit thereby serves as a stable surrogate for the diphosphate. They demonstrate that isoprenoid (phosphinylmethyl)phosphonates (PMPs) are effective inhibitors of squalene synthetase, binding to the enzyme with affinity comparable to FPP itself.

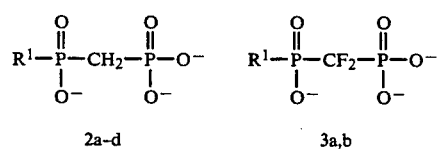

2a-d      3a,b $R^1$

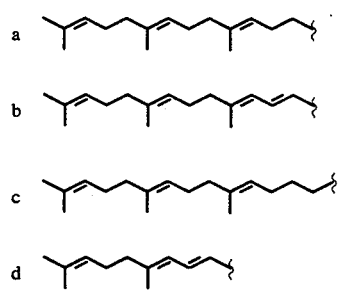

a b c d

DESCRIPTION OF THE INVENTION

In accordance with the present invention, there is provided phosphorus-containing isoprenoid phosphinylformic acid compounds which inhibit cholesterol biosynthesis, and thus are useful as hypocholesterolemic and antiatherosclerotic agents and have the following structure

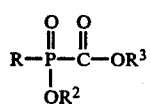

I wherein
$R^2$ is a metal ion, lower alkyl or H;
$R^3$ is a metal ion or lower alkyl;
R is $R^1-(CH_2)-$, $R^1-(CH_2)_m O-$ or $R^1-(CH_2)_mOCH_2-$, wherein n is 1 to 4, m is 0 to 3; and $R^1$ is $R^5$-$Q^1$-$Q^2$-$Q^3$- wherein $Q^1$, $Q^2$ and $Q^3$ are independently:

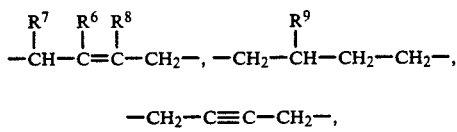

or a bond, with the stipulation that if $Q^1$ is a bond, then $Q^2$ and $Q^3$ must be bonds, and if $Q^2$ is a bond, then $Q^3$ is a bond; $R^6$ is H, lower alkyl, fluoro or fluoroalkyl (e.g. $CH_2F$, $CF_3$); $R^7$ is H, fluoro, lower alkyl or alkylthio; $R^8$ is H, fluoro, trimethylsilyl or lower alkyl; $R^9$ is H, or lower alkyl;

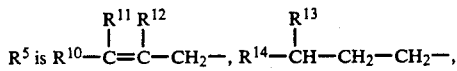

$R^{16}-C\equiv C-CH_2-$ (wherein $R^{16}$ is lower alkyl or H), or $CH_3(CH_2)_p-$ where p is 2 to 7; $R^{10}$ and $R^{11}$ are independently hydrogen, lower alkyl such as methyl or ethyl, fluoro, lower alkenyl or fluoroalkyl or $R^{10}$ and $R^{11}$ can be taken together to form $(CH_2)_s$, where s is 2 to 7; $R^{12}$ is hydogen, lower alkyl, fluoro or lower alkenyl; $R^{13}$ and $R^{14}$ are independently lower alkyl such as methyl or ethyl; with the proviso that if all of $Q^1$, $Q^2$ and $Q^3$ are bonds, then $R^{10}$ and $R^{11}$ cannot both be H, and $R^5$ cannot be $CH_3(CH_2)_p-$, with p<4.

The formula I compounds of the invention include all stereoisomers thereof.

Unless otherwise indicated, the term "lower alkyl" or "alkyl" as employed herein alone or as part of another group includes both straight and branched chain hydrocarbons containing 1 to 8 carbons in the normal chain, preferably 1 to 4 carbons, such as methyl, ethyl, propyl, isopropyl, butyl, t-butyl, isobutyl, pentyl, hexyl or isohexyl.

The term "lower alkenyl" or "alkenyl" as used herein by itself or as part of another group refers to straight or branched chain radicals of 2 to 12 carbons, preferably 3 to 6 carbons in the normal chain, which include one double bond in the normal chain, and which may include an aryl or alkyl substituent, such as vinyl, 2-propenyl, 2-butenyl, 3-phenyl-2-propenyl, 2-pentenyl, 2-hexenyl, 2-heptenyl, 2-octenyl, 2-nonenyl, 2-decenyl, 2-undecenyl, 2-dodecenyl and the like.

The term "halogen" or "halo" as used herein refers to chlorine, bromine, fluorine, and iodine.

The term "haloalkyl" as used herein refers to any of the lower alkyl groups defined above substituted with a halogen as defined above, for example $CH_2F$, $CF_3$ and the like.

The term "metal ion" refers to alkali metal ions such as sodium, potassium or lithium and alkaline earth metal ions such as magnesium and calcium.

Thus, the compounds of formula I of the invention include the following types of compounds:

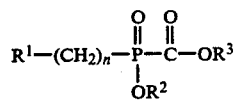 IA

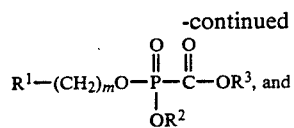 IB

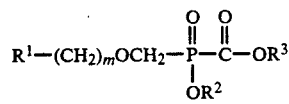 IC

Preferred are those compounds of formula I, IA, IB and IC wherein $R^1$ is

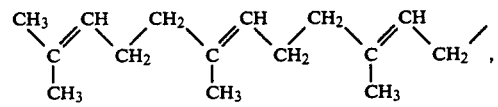

n is 1, 2 or 3, m is 1 or 2, $R^2$ is H or a metal ion, and $R^3$ is lower alkyl, a metal ion or H.

The compounds of the invention may be prepared according to the following reaction sequences.

Scheme I
Preparation of compound IA

II

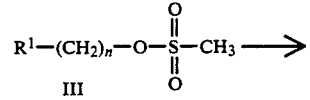
III

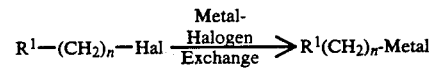
IV            A

Hal = Br or I

A

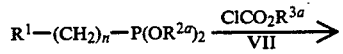
B

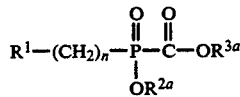

ID ($R^{2a}$, $R^{3a}$ = lower alkyl)

(1) TMSI or TMSBr
(2) 1 equiv $^\ominus$OH (1) TMSI or TMSBr
(2) excess $^\ominus$OH
or
excess $^\ominus$OH

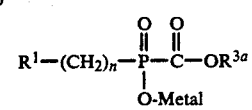
IE

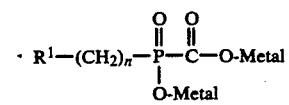
IF

Acid

-continued
Scheme I
Preparation of compound IA

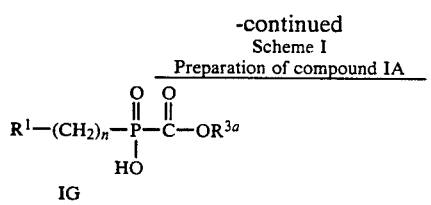

IG

The resulting mesylate III is treated with a metal halide such as lithium bromide in tetrahydrofuran or sodium iodide in acetone while heating to a temperature within the range of from about 45 to about 65° C. to form the halide IV $$R^1-(CH_2)_n-Hal\ (Hal=Br\ or\ I).\qquad IV$$

Halide IV is then subjected to a Grignard reaction, for

Scheme II
Alternative Synthesis of Compounds IA (that is, ID through IG) and IC (that is ID$^1$ through IG$^1$)

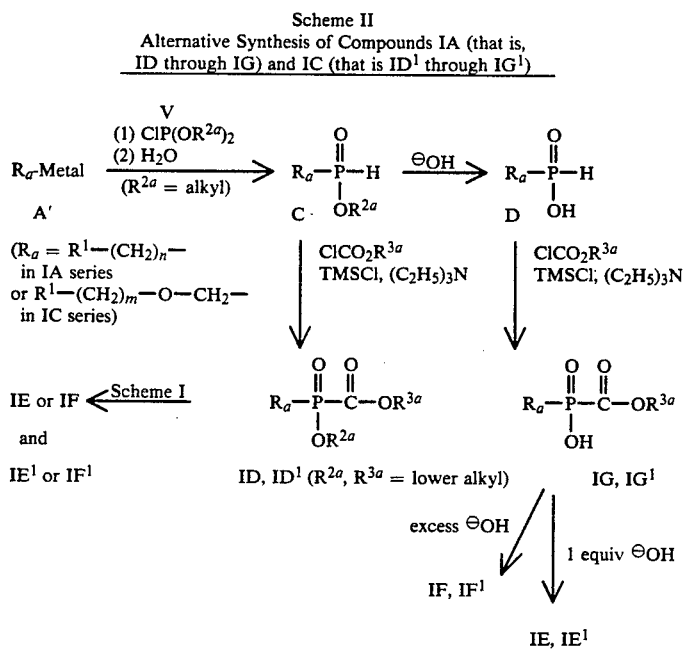

Scheme III
Preparation of Compound IB
($R^3$ = lower alkyl)

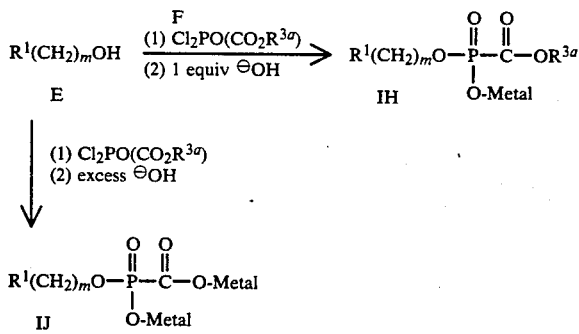

As seen in Reaction Scheme I, compounds of the invention of formula IA may be prepared starting with the alcohol II wherein R is $R^1-(CH_2)_n-$, that is $$R^1-(CH_2)_n-OH \qquad II$$

which is converted to the corresponding mesylate by treating II with mesyl chloride, organic base such as triethylamine, in an organic solvent such as methylene chloride, to form the mesylate

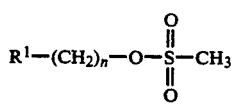

example, by treating IV with a stirred suspension of magnesium turnings and 1,2-dibromoethane, in the presence of diethyl ether under an inert atmosphere such as argon, to form a Grignard solution referred to in Reaction Scheme I as R-Metal    A wherein R is $R^1-(CH_2)_n-$.

Alternatively, R-Metal (R=lithium) is prepared by treating IV with an alkyl lithium such as n-butyl or t-butyllithium or lithium metal, in diethyl ether or tetrahydrofuran at a temperature of from about −78° C. to about 25° C., with a ratio of alkyllithium or lithium metal to IV of from about 1:1 to about 2.5:1.

The anion solution is reacted with phosphite V

ClP—(OR$^{2a}$)$_2$           V (wherein R$^{2a}$ is lower alkyl) in the presence of an organic solvent such as diethyl ether or tetrahydrofuran, under an inert atmosphere such as argon, at a temperature within the range of from about −78° C. to about 25° C., employing a molar ratio of V:A of within the range of from about 1:1 to about 4:1, to form the phosphonite B R$^1$—(CH$_2$)$_n$—P(OR$^{2a}$)$_2$.      B Phosphonite B is treated with a chloroformate VII ClCO$_2$R$^{3a}$           VII (wherein R$^{3a}$ is lower alkyl) such as ethyl chloroformate, employing a molar ratio of VII:B of within the range of from about 1:1 to about 10:1, to form the diester of the invention ID. Diester ID, in an inert organic solvent such as methylene chloride, may then be subjected to dealkylation by treating with excess bromotrimethylsilane (TMSBr) or iodotrimethylsilane (TMSI) in the presence of 2,4,6-collidine or bis(trimethylsilyl)trifluoroacetamide and then treating with one equivalent of a strong inorganic base such as aqueous NaOH, KOH, LiOH or Mg(OH)2, optionally in the presence of an alcohol such as methyl alcohol, to form the salt IE or with excess strong base (greater than two equivalents) to form the salt IF. The salt IE may be treated with strong acid such as HCl to form the free acid IG.

Compounds of the invention of formula IC may be prepared employing the Reaction Scheme I except that the starting alcohol II is treated with a solution of base such as potassium hydride or sodium hydride and then with an iodide of the structure VIII I—CH$_2$—Sn(n—C$_4$H$_9$)$_3$      VIII employing a molar ratio of VIII:II of within the range of from about 1:1 to about 1.5:1, in the presence of an inert organic solvent such as tetrahydrofuran, diethylether or dimethyl formamide to form the stannane of the structure IX R$^1$—(CH$_2$)$_m$—O—CH$_2$—Sn(n—C$_4$H$_9$)$_3$.      IX The stannane IX is dissolved in an inert organic solvent such as diethyl ether or tetrahydrofuran, cooled to a temperature within the range of from about −90° C. to about 0° C., while under an inert atmosphere such as argon, and treated with a strong base such as n-butyllithium in diethyl ether, tetrahydofuran or other inert organic solvent, under an inert atmosphere such as argon. The resulting solution is then used in place of the anion solution A in Scheme I, as described above, to form the phosphite B$^1$ R$^1$—(CH$_2$)$_m$—O—CH$_2$—P(OR$^{2a}$)$_2$,      B$^1$ the diester ID$^1$ $$R^1-(CH_2)_m-O-CH_2-\underset{\underset{OR^{2a}}{|}}{\overset{\overset{O}{\|}}{P}}-\overset{\overset{O}{\|}}{C}-OR^{3a}$$    ID$^1$ (wherein R$^{2a}$ and R$^{3a}$ are lower alkyl), and the salts IE$^1$ and IF$^1$ $$R^1-(CH_2)_m-O-CH_2-\underset{\underset{O\text{-Metal}}{|}}{\overset{\overset{O}{\|}}{P}}-\overset{\overset{O}{\|}}{C}-OR^{3a}$$    IE$^1$ and $$R^1-(CH_2)_m-O-CH_2-\underset{\underset{O\text{-Metal}}{|}}{\overset{\overset{O}{\|}}{P}}-\overset{\overset{O}{\|}}{C}-O-\text{Metal}$$    IF$^1$ and the free acid IG$^1$ $$R^1-(CH_2)_m-O-CH_2-\underset{\underset{OH}{|}}{\overset{\overset{O}{\|}}{P}}-\overset{\overset{O}{\|}}{C}-OR^{3a}$$    IG$^1$ In an alternative synthesis, as seen in Reaction Scheme II, compounds of formula IA or IC of the invention may be prepared by treating A'

R$_a$-Metal           A' wherein R$_a$ is R$^1$—(CH$_2$)$_n$— or R$^1$—(CH$_2$)$_m$O—CH$_2$— (prepared as described above) with phosphite V, employing the procedure as set out above with respect to Scheme I, employing a molar ratio of V:A' of within the range of from about 1:1 to about 5:1.

The reaction mixture is quenced with deaerated water to form the phosphonous ester C $$R_a-\underset{\underset{OR^{2a}}{|}}{\overset{\overset{O}{\|}}{P}}-H$$    C (where R$^{2a}$ is lower alkyl) which is a novel intermediate.

The phosphonous ester C may then be treated with a chloroformate VII in the presence of chlorotrimethylsilane, and an organic base such as triethylamine or diisopropylethylamine to form the diester ID, ID$^1$. ID may be converted to IE or IF, and ID$^1$ may be converted to IE$^1$ and IF$^1$ according to Scheme I.

The phosphonous ester C may be directly hydrolyzed by treatment with a strong base such as potassium hydroxide, sodium hydroxide or lithium hydroxide optionally in the presence of an organic solvent such as methanol, ethanol or tetrahydrofuran, and the resulting salt is treated with a strong acid such as dilute hydrochloric acid or dilute sulfuric acid to form phosphonous acid D $$R_a-\underset{\underset{OH}{|}}{\overset{\overset{O}{\|}}{P}}-H$$    D which is a novel intermediate.

The phosphonous acid D may be treated with a chloroformate VII in the presence of chlorotrimethylsilane, and an organic base, such as triethylamine or diisopropylethylamine to form the monoester IG, IG$^1$

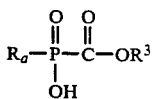

The monoester IG, IG$^1$ may be converted to the corresponding monometal salt IE or IE$^1$ or dimetal salt IF or IF$^1$ by treating with one equivalent of base or excess base respectively, as described hereinbefore with respect to Reaction Scheme I.

Referring to Reaction Scheme III, compounds of the invention of formula IB may be prepared starting with alcohol

$$R^1-(CH_2)_m OH \qquad E$$

which is treated with dichlorophosphinylformate ester F

(where R$^{3a}$ is lower alkyl) in the presence of an organic solvent such as tetrahydrofuran, diethyl ether or dichloromethane, under an inert atmosphere such as argon, at a temperature within the range of from about −80 to about 0° C., employing a molar ratio of F:E of within the range of from about 1:1 to about 5:1.

Where it is desired to form the monosalt IH, the reaction mixture is treated with one equivalent of base such as sodium hydroxide or potassium hydroxide. Where the dimetal salt IJ is desired, the reaction mixture is treated with excess base.

The alcohol starting material II or E where m is 1 or n is 1, that is E$^1$

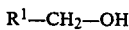
$$R^1-CH_2-OH \qquad E^1$$

may be prepared according to the following reaction sequence (following the procedure of E. J. Leopold, *Organic Synthesis* 1985, 64, pp 164–173)

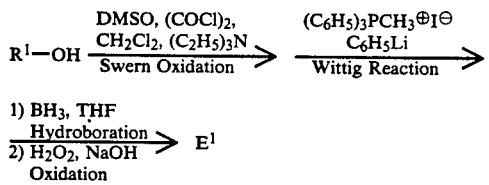

The alcohol starting material II or E where m is 2 or n is 2 that is E$^2$

$$R^1-CH_2CH_2-OH \qquad E^2$$

may be prepared according to the following reaction sequence:

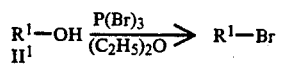

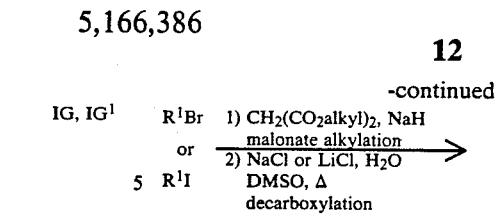

$$R^1-CH_2CO_2\text{alkyl} \xrightarrow[\text{Reduction}]{\underset{(C_2H_5)_2O}{LiAlH_4}} E^2$$

II$^2$

The alcohol starting material II or E where m is 3 or n is 3, that is II$^3$

$$R^1-CH_2CH_2CH_2-OH \qquad II^3$$

may be prepared according to the following reaction sequence

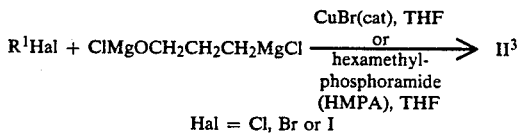

Hal = Cl, Br or I

The alcohol starting material where n=4, that is

$$R^1-CH_2CH_2CH_2CH_2-OH \qquad II^4$$

may be prepared according to the following reaction sequence

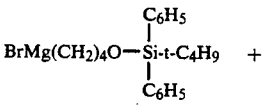

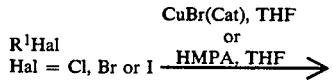

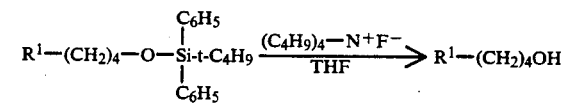

Examples of starting material II or E that is R$^1$—(CH$_2$)$_m$ or $_n$—OH and m is 0, 1, 2 or 3 and n is 1, 2, 3 or 4 suitable for use herein include the following which are either known in the literature or are simple derivatives of known compounds prepared by employing conventional procedures.

It will be appreciated that the compounds listed in the following table represent all possible stereoisomers.

| R$^1$—(CH$_2$)$_m$ or $_n$ —OH (m is 0 to 3, n is 1 to 4) where R$^1$ is R$^5$—Q$^1$—Q$^2$—Q$^3$— as follows in A. through F. |
|---|

A.

(structure shown)

| | R$^{10}$ | R$^{11}$ |
|---|---|---|
| 1. | C$_2$H$_5$ | CH$_3$ |
| 2. | CH$_3$ | C$_2$H$_5$ |
| 3. | n-C$_3$H$_7$ | CH$_3$ |

5,166,386

13

-continued

| R¹—(CH₂)ₘ or ₙ —OH (m is 0 to 3, n is 1 to 4) where R¹ is R⁵—Q¹—Q²—Q³— as follows in A. through F. | | |
|---|---|---|
| 4. | CH₃ | n-C₄H₉ |
| 5. | t-C₄H₉ | CH₃ |
| 6. | —(CH₂)ₛ'— s' = 4 to 6 | |
| 7. | H | H |
| 8. | F | F |
| 9. | CH₂F | CH₃ |
| 10. | —CH=CH₂ | H |

B. 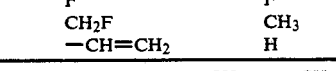

alkyl-(CH₂)ₚ—

1. CH₃(CH₂)ₚ—  where p is 3 to 7

2. (CH₃)₂C—(CH₂)ₚ—  where p is 2 to 4

C. 1. CH₃—C(CH₃)=C—CH₂—(CH₂—C(CH₃)=C—CH₂)ₑ
q = 0, 1, 2, 3

2. H—C(CH₃)—CH₂—CH₂—(CH₂—CH(CH₃)—CH₂—CH₂)ₑ
q = 0, 1, 2, 3

D. R¹ is CH₃—C(R¹¹)=CH—CH₂—CH₂—C(R⁶)=CH—CH₂—CH₂—C(R⁶')=CH—CH₂—

| | R¹¹ | R⁶ | R⁶' |
|---|---|---|---|
| 1. | C₂H₅ | C₂H₅ | CH₃ |
| 2. | CH₃ | CH₃ | C₂H₅ |
| 3. | CH₃ | C₂H₅ | C₂H₅ |
| 4. | C₂H₅ | C₂H₅ | C₂H₅ |
| 5. | CH₃ | C₂H₅ | CH₃ |
| 6. | CH₃ | H | CH₃ |
| 7. | CH₃ | CH₃ | H |
| 8. | H | H | H |
| 9. | CH₃ | CH₃ | H |
| 10. | H | H | H |

E. R¹ is CH₃—C(CH₃)=CH—CH₂—CH₂—C(CH₃)=CH—CH₂—CH(R⁷)—C(R⁶)=C(R⁸)—CH₂—

| | R⁷ | R⁶ | R⁸ |
|---|---|---|---|
| 1. | H | F | H |
| 2. | H | H | F |
| 3. | H | CH₃ | CH₃ |
| 4. | CH₃S | CH₃ | H |
| 5. | F | CH₃ | H |
| 6. | CH₃ | CH₃ | H |
| 7. | H | CH₃ | CH₃ |
| 8. | H | CF₃ | H |
| 9. | H | F | H |
| 10. | H | CH₃ | (CH₃)₃Si |
| 11. | H | CH₃ | F |

F. Other examples of R¹ include the following

14

-continued

R¹—(CH₂)ₘ or ₙ —OH (m is 0 to 3, n is 1 to 4) where R¹ is R⁵—Q¹—Q²—Q³— as follows in A. through F.

1. 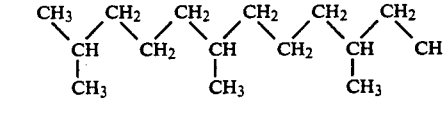

2. 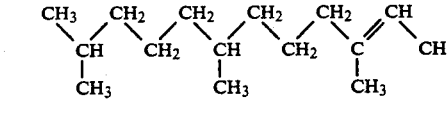

3. 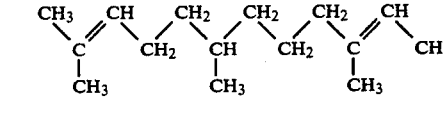

4. 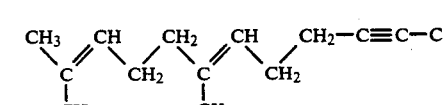

5. 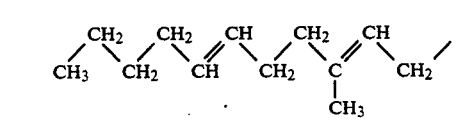

6. 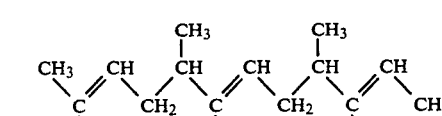

7. 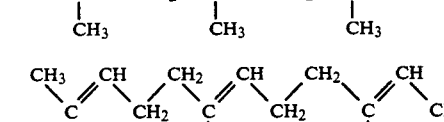

8. 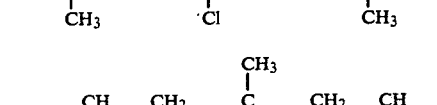

9. 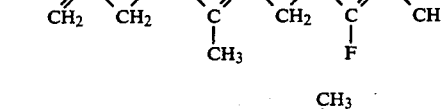

10. 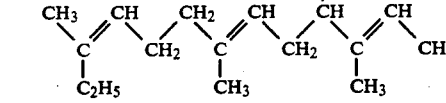

11. 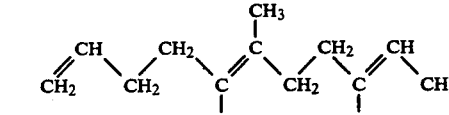

12. 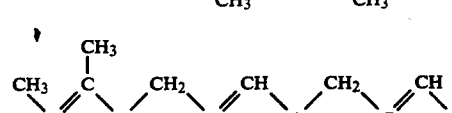

-continued

R$^1$—(CH$_2$)$_m$ or $_n$ —OH (m is 0 to 3, n is 1 to 4) where
R$^1$ is R$^5$—Q$^1$—Q$^2$—Q$^3$— as follows in A. through F.

13.
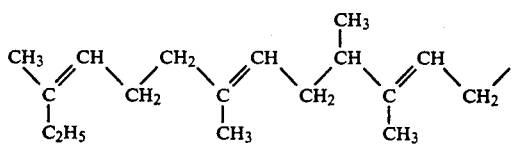

14.
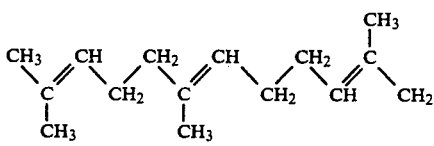

15.
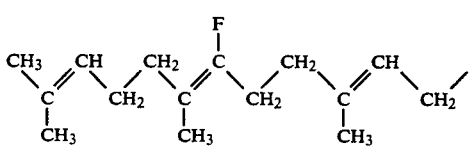

16.
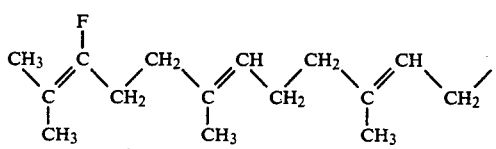

The compounds of Formula I of the invention inhibit cholesterol biosynthesis by inhibition of de novo squalene production. These compounds inhibit the squalene synthetase enzyme and, in addition, some of the compounds of Formula I of the invention inhibit other enzymes in the pathway from isopentenyl diphosphate to squalene, that is, farnesyl diphosphate synthetase and isopentenyl diphosphate-dimethylallyl diphosphate isomerase.

Thus, the compounds of the invention are useful in treating atherosclerosis to inhibit progression of disease and in treating hyperlipidemia to inhibit development of atherosclerosis. In addition, the compounds of the invention may increase plasma high density lipoprotein cholesterol levels.

As squalene synthetase inhibitors, the compounds of the invention may also be useful in inhibiting formation of gallstones and in treating tumors.

The compounds of the invention may also be employed in combination with an antihyperlipoproteinemic agent such as probucol and/or with one or more serum cholesterol lowering agents such as Lopid (gemfibrozil), bile acid sequestrants such as cholestyramine, colestipol, polidexide (DEAE-Sephadex) as well as clofibrate, nicotinic acid and its derivatives, neomycin, p-aminosalicyclic acid, bezafibrate and the like and/or one or more HMG CoA reductase inhibitors such as lovastatin, pravastatin, velostatin or simvastatin.

The above compounds to be employed in combination with the squalene synthetase inhibitor of the invention will be used in amounts as indicated in the Physicians' Desk Reference (PDR).

Inhibition of squalene synthetase may be measured by the following procedure.

Rat liver microsomal squalene synthetase activity is measured using farnesyl diphosphate as substrate and quantitating squalene synthesis using gas chromatographic analysis. The assay was developed by modifying conditions originally described by Agnew (Methods in Enzymology 110:357, 1985).

Preparation of Rat Liver Microsomes

Livers are dissected from 2 or 3 decapitated Sprague Dawley rats and are quickly transferred to ice cold buffer (potassium phosphate, 0.05M, (pH 7.4); MgCl$_2$, 0.004M; EDTA, 0.001M; and 2-mercaptoethanol 0.01M) and rinsed thoroughly. The livers are minced in cold buffer (2.0 ml/g) and homogenized using a Potter-Elvejhem homogenizer. The homogenate is centrifuged at 5,000×g, 10 minutes (4° C.), and the supernatant poured through 2 layers of cheese cloth. The supernatant is then centrifuged at 15,000×g for 15 minutes (4°). Again the supernatant is filtered through 2 layers of cheese cloth, and centrifuged a third time at 100,000×g for 1.0 hour at 4° C. Following centrifugation the microsomal pellet is resuspended in a volume of buffer equivalent to 1/5 the volume of the original homogenate, and homogenized in a ground glass homogenizer. Aliquotted microsomes are frozen at −80° C., and retain activity for at least two months.

Enzyme Assay

Reaction Mixtures are prepared in 50 ml round bottom pyrex glass tubes with tight-fitting, teflon-lined, screw caps. Tubes are cooled to 4° C., and the following components are added in sequence:

| | |
|---|---|
| 1. Potassium phosphate buffer 0.275 M, pH 7.4) | 0.36 ml |
| 2. KF (55 mM) | 0.36 ml |
| 3. NADPH (5.0 mM, freshly prepared) | 0.36 ml |
| 4. H$_2$O (or H$_2$O + test compound) | 0.16 ml |
| 5. MgCl$_2$ (27.5 mM) | 0.36 ml |
| 6. Microsomal Enzyme (0.48 mg microsomal protein in homogenization buffer) | 0.20 ml |
| | 1.8 ml |

This mixture is equilibrated under N$_2$ at 4° C. for 5–15 minutes. Reaction mixtures are then warmed to 30° C., and the enzyme reaction initiated by adding 0.2 ml of farnesyl pyrophosphate (219μM) prepared in H$_2$O. Each tube is again overlayered with N$_2$, and incubated at 30° C. for 60 minutes. The reaction is stopped by the addition of 1.0 ml KOH (40%). Ethanol (95%) (spectral grade) (1.0 ml) is added to each tube. Docosane (5 nmoles in hexane) is added to each tube as an internal standard. The mixture is saponified at 65° C. for 30 minutes. The tubes are cooled to room temperature and extracted twice with 10.0 ml spectral grade hexane.

The upper organic phase fractions are pooled in glass 20.0 ml scintillation vials and reduced in volume to ≃1.0 ml under a stream of N$_2$. The sample is then transferred to acid-washed, conical bottom, glass (1.0 ml) microvials, and brought to dryness under N$_2$. The residue is resuspended in 50 μl hexane (spectral grade), and these samples are spun at 1000 rpm at room temperature for 10 minutes. Following centrifugation approximately 40 μl of supernatant is transferred to 100 μl acid-washed microvials with septa/crimp-top caps (compatible with the Hewlett-Packard GC auto injector).

Gas Chromatography

Two μL of each sample is injected onto a fused silica megabore DB-17 column (15M×0.525 mm) (J&W Scientific) using a splitless mode of injection. Gas flow rates are listed below:

| Make up gas (helium) | 20 ml/min. |
|---|---|
| Air | 400 ml/min. |
| Hydrogen | 30 ml/min. |
| Carrier (helium) | 15 ml/min. |
| Septum purge vent | 5 ml/min. |
| | (Septum purge off 0.00 min., on at 0.5 min.) |

The injector temperature is 200° C., and the FID detector temperature is set at 270° C. Oven temperature is programmed through a two ramp sequence as follows:

| Oven: |
|---|
| Initial temperature 180° C., initial time 10 minutes |
| Ramp one: 20° C./minute |
| Second temperature 250° C., second time 10 minutes |
| Ramp two: 20° C./minute |
| Third temperature 260° C., third time 10 minutes |
| (Equilibration time 1.0 minute) |

Using this gas chromatographic system, docosane (internal standard) has a retention time of 3.6-3.7 minutes, and squalene has a retention time of 14.7-14.9 minutes. The amount of squalene in each reaction mixture is determined by obtaining the areas under the squalene and docosane peaks and using the following formula to calculate the amount of squalene (nmoles) in the total reaction mixture.

Squalene (nmoles/reaction mixture) = 5.0 (nmoles docasane × internal standard) $\frac{\text{Squalene Peak Area}}{\text{Docasane Peak Area}} \times RR^*$

*RR = Response Ratio [Docasane/Squalene]
*RR = 0.56

Compounds Testing

Compounds are dissolved in $H_2O$ and added to reaction mixtures prior to addition of farnesyl pyrophosphate substrate. All reaction mixtures are run in duplicate, at several concentrations. Additionally, all compound $I_{50}$ values are derived from composite dose response data.

A further aspect of the present invention is a pharmaceutical composition consisting of at least one of the compounds of Formula I in association with a pharmaceutical vehicle or diluent. The pharmaceutical compostion can be formulated employing conventional solid or liquid vehicles or diluents and pharmaceutical additives of a type appropriate to the mode of desired administration. The compounds can be administered to mammalian species including humans, monkeys, dogs, etc. by an oral route, for example, in the form of tablets, capsules, granules or powders, or they can be administered by a parenteral route in the form of injectable preparations. The dose for adults is preferably between 200 and 2,000 mg per day, which can be administered in a single dose or in the form of individual doses from 1-4 times per day.

A typical capsule for oral administration contains active ingredient (250 mg), lactose (75 mg) and magnesium stearate (15 mg). The mixture is passed through a 60 mesh sieve and packed into a No. 1 gelatin capsule.

A typical injectible preparation is produced by asceptically placing 250 mg of sterile active ingredient into a vial, asceptically freeze-drying and sealing. For use, the contents of the vial are mixed with 2 ml of physiological saline, to produce an injectible preparation.

The following Examples represent preferred embodiments of the present invention.

Introduction to Experimental

All temperatures are reported in degrees Centigrade. $^1H$ and $^{13}C$ chemical shifts are reported as $\delta$-values with respect to $Me_4Si$ ($\delta=0$). $^{31}P$ spectra were measured on a JEOL FX90Q FT-NMR spectrometer at 36.2 MHz, utilizing the $^1H$ decoupled mode. The $^{31}P$ data were obtained using 85% $H_3PO_4$ as an external reference ($\delta=0$). Coupling constants J are reported in Hz. Chemical ionization mass spectra (CI-MS) were determined with a Finnigan TSQ-4600 instrument equipped with a direct exposure probe using the indicated reagent gases. Fast atom bombardment mass spectra (FAB-MS) were recorded on a VG Analytical ZAB-2F spectrometer. Ions were sputtered (8keV Xe) from a matrix containing dithiothreitol, dithioerythritol, DMSO, glycerol and water.

All reactions were carried out under an atmosphere of dry argon or nitrogen. The following reagents and solvents were distilled prior to use from the indicated drying agents, where applicable: $CH_2Cl_2$, 2,4,6-collidine, and diisopropylamine ($CaH_2$); THF and diethyl ether (K, benzophenone); N,N-diethyltrimethylsilylamine and oxalyl chloride. Benzene was passed through neutral alumina (activity I) and stored over 4A-molecular sieves. Lithium bromide was dried at 100° C. over $P_2O_5$. (E,E)-Farnesol was purchased from Aldrich Chemical Company.

TLC was performed on E. Merck Silica Gel 60 F-254 plates (0.25 mm) or E. Merck Cellulose F plates (0.1 mm). Flash chromatography was carried out using E. Merck Kieselgel 60 (230-400 mesh).

Reverse-phase chromatographic purification of PMP salts was carried on CHP20P gel (75-150 μ), a highly porous, polystyrene-divinyl benzene copolymer available from Mitsubishi Chemical Industries. The indicated general procedure was followed: An FMI Model RP-SY pump was utilized for solvent delivery. A column of CHP20P (2.5 cm diameter, 12-22 cm height) was slurry packed and washed with water (500-1000 mL), and a basic, aqueous solution of the crude salt was applied to the top of the column. Typically, the column was eluted with water, followed by a gradient composed of increasing concentrations of acetonitrile or methanol in water. The gradient was created by placing the tip of a tightly stoppered separatory funnel containing 300-500 mL of the organic solvent, or an aqueous-organic mixture, just beneath the surface of a reservoir containing 300-500 mL of pure water. To start the gradient, the stopcock of the separatory funnel was opened, so that as the solvent was withdrawn by the pump from the reservoir, it was replaced with the solvent from the separatory funnel. HPLC-grade solvents and Lectrostill steam distilled water were employed. Fractions were collected (10-15 mL each) at a flow rate of 5-10 mL per minute. Those fractions that contained pure product as judged by TLC were pooled, the organic solvents were evaporated and the aqueous residue was lyophilized to dryness.

EXAMPLE 1

(E,E)-[Ethoxy(5,9,13-trimethyl-4,8,12-tetradecatrienyl)phosphinyl]formic acid, ethyl ester

A. Bishomofarnesol (1) (E,E)-3,7,11-Trimethyl-2,6,10-dodecatrienyl bromide

A solution of 1.00 g (4.5 mmol) of (E,E)-farnesol (Aldrich, further purified by flash chromatography) in 10 ml of distilled diethyl ether at 0° C. under argon in the dark was treated dropwise with a solution of 195 μL (2.05 mmol, 0.45 eq.) of $PBr_3$ in 2 ml of diethyl ether. The resultant mixture was stirred at 0° C. for one hour, then quenched with water and separated. The organic phase was washed with 5 ml of $H_2O$, 5 ml of saturated $NaHCO_3$, and 5 ml of brine, dried over $Na_2SO_4$ and evaporated to give 1.26 g (98%) of crude bromide as a clear oil.

TLC Silica (2:8 ethyl acetate:hexane) $R_f$=0.69.

$^1$H NMR ($CDCl_3$, 270 MHz): δ 5.52 (t, 1H, J=8.5 Hz), 5.08 (m, 2H), 4.01 (d, 2H, J=8.5 Hz), 1.9–2.2 (m, 8H), 1.73 (s, 3H), 1.68 (s, 3H), 1.60 (s, 6H) ppm.

(2) (E,E)-5,9,13-Trimethyl-4,8,12-tetradecatrienoic acid, 1,1-dimethylethyl ester To a solution of 9.60 ml (68.5 mmol, 1.5 eq.) of diisopropylamine in 100 ml of THF at −78° C. under argon was added 28.2 ml (45.0 mmol, 1.0 eq.) of 1.6M n-butyllithium in hexanes over 20 minutes. After warming to 0° C. for 15 minutes, the solution was recooled to −78° C. and 6.05 ml (45 mmol, 1.0 eq) of t-butyl acetate was added over 20 minutes. After an additional 15 minutes, 16.0 ml (92 mmol, 2.05 eq.) of hexamethylphosphoramide (HMPA) was added, followed by a solution of 12.53 g (45.0 mmol) of Part A(1) farnesyl bromide in 100 ml of THF over 20 minutes. The reaction was stirred at −78° C. for 2.5 hours, quenched with saturated $NH_4Cl$ and allowed to warm to room temperature. After diluting with 400 ml of ethyl acetate, the mixture was washed with four 100 ml portions of water, and 200 ml of brine, dried over $MgSO_4$ and evaporated to provide 12.96 g of crude product as a yellow oil. Purification by flash chromatography on 1 kg of silica gel, eluted with 1:9 ethyl acetate:petroleum ether afforded 9.39 g (65%) of title compound as a pale yellow oil.

TLC Silica gel (2:98 ethyl acetate:hexane) $R_f$=0.16.

IR(neat) 2977, 2925, 2857, 1733, 1452, 1368, 1258, 1149 cm$^{-1}$.

$^1$H NMR($CDCl_3$, 270 MHz): δ 5.10 (m, 3H), 2.25 (m, 4H), 1.9–2.1 (m, 8H), 1.68 (s, 3H), 1.62 (s, 3H), 1.59 (s, 6H), 1.44 (s, 9H) ppm.

Mass Spec (CI-$CH_4$/$N_2O$) (+ ions) m/e 165 (M+H-$C_4H_8$), 247, 183, 137, 68, 57. (− ions) m/e 319 (M-H), 279, 251, 100.

(3) Bishomofarnesol

To a stirred solution of 5.00 g (15.6 mmol) of Part (2) compound in 45 ml of dry diethyl ether at 0° C. under argon was added 592 mg (15.6 mmol, 1 mol - eq.) of lithium aluminum hydride, and the resulting suspension was stirred at room temperature for 20 hours. After cooling to 0° C., the reaction was quenched by treating with 5 ml of $H_2O$, 5 ml of 15% NaOH, and 15 ml of $H_2O$ and stirring the suspension for ½ hour. After adding $Na_2SO_4$, the slurry was filtered through Celite, washing well with diethyl ether and evaporated to obtain 3.62 g of crude product. Purification by flash chromatography on 300 g of silica gel, eluted with 1:9 ethyl acetate:petroleum ether provided 3.516 g (90%) of bishomofarnesol as a colorless liquid.

TLC Silica gel (2:8 ethyl acetate:hexane) $R_f$=0.19

IR(neat) 3330, 2964, 2926, 2873, 2958, 1448, 1384, 1107, 1059, 401 cm$^{-1}$.

$^1$H NMR($CDCl_2$, 270 MHz): δ 5.10 (m, 3H), 3.63 (t, 2H, J=6.5 Hz), 1.9–2.2 (m, 10H), 1.68 (s, 3H), 1.62 (2, 3H), 1.60 (s, 7H) ppm.

Mass Spec (CI-$CH_4$/$N_2O$, + ions) m/e 251 (M+H), 249 (M+H-$H_2$), 137, 123, 109, 69.

B. (E,E)-5,9,13-Trimethyl-4,8,12-tetradecatrien-1-ol, methanesulfonate ester To a stirred solution of 2.02 g (8.07 mmol) of bishomofarnesol (prepared as described in Example 1, Part A) in 20 mL of dichloromethane at 0° C. was added 2.2 mL (16.1 mmol) of triethylamine followed by 0.69 mL (8.90 mmol) of methanesulfonyl chloride, dropwise over 15 minutes. After stirring for 1.5 hours at 0° C., the reaction was diluted with dichloromethane, washed with 20 mL each of 10% HCl, saturated $NaHCO_3$ and brine, dried ($MgSO_4$) and evaporated to give 2.71 g ("100%") of the crude title mesylate as a colorless oil.

TLC Silica gel ($CH_2Cl_2$) $R_f$=0.46.

$^1$H NMR ($CDCl_3$, 270 MHz): δ 5.09 (t, 3H, J=6.5 Hz), 4.21 (t, 2H, J=7.0 Hz), 2.99 (s, 3H), 1.9–2.2 (m, 10H), 1.78 (quint, 2H, J=7.0 Hz), 1.65 (s, 3H), 1.61 (s, 3H), 1.60 (s, 6H).

C.

(E,E)-16-Bromo-2,6,10-trimethyl-2,6,10-tetradecatriene

To a solution of 2.56 g (7.79 mmol) of Part B mesylate in 15 mL of THF at room temperature was added 2.02 g (23.37 mmol) of anhydrous lithium bromide, resulting in a mild exotherm. For this purpose, lithium bromide was dried at 100° C. over $P_2O_5$ under vacuum. The suspension was allowed to stir for 23 hours at room temperature, when it was diluted with diethyl ether, washed with water (two portions) and brine, dried ($MgSO_4$) and evaporated to provide 2.29 g of a pale yellow liquid. Flash chromatography on 65 g of silica gel eluted with petroleum ether gave 2.22 g (91%) of title bromide as a colorless liquid.

TLC Silica gel (hexane) $R_f$=0.35.

IR(neat) 2965, 2926, 2856, 1666, 1440, 1383, 1249, 1109 cm$^{-1}$.

$^1$H NMR($CDCl_2$, 270 MHz): δ 5.10 (br, 3H), 3.39 (t, 2H, J=6.5 Hz), 1.8–2.3 (m, 12H), 1.68 (s, 3H), 1.63 (s, 3H), 1.60 (s, 6H) ppm.

Mass Spec (CI-$CH_4$/$N_2O$, + ions) m/e 315, 313 (M+H), 313, 311 (M+H-$H_2$).

D. (E,E)-[Ethoxy(5,9,13-trimethyl-4,8,12-tetradecatrienyl)phosphinyl]formic acid, ethyl ester To a stirred suspension of 200 mg (8.22 mmol) of Mg turnings in 3 mL of diethyl ether under argon was added 30 μL (0.35 mmol) of 1,2-dibromoethane, followed 10 minutes later by the dropwise addition of 1.26 g (4.02 mmol) of Part C bromide in 5 mL of diethyl ether over 25 minutes. The mixture was stirred for an hour while occasionally warming to reflux with a warm water bath. The mixture was then sonicated for 40 minutes, followed by stirring at room temperature for an additional hour. The Grignard solution was cannulated into an addition funnel of a second apparatus, fitted with a glass wool plug above the stopcock to remove any particulates in the solution. The Grignard solution was added dropwise over 30 minutes to a stirred solution of 0.58 mL (4.02 mmol) of diethyl chlorophosphite in 5 mL of diethyl ether at 0° C. The resulting suspension was stirred at 0° C. for 15 minutes followed by room temperature for one hour. The suspension was cannulated into a Schlenk filter packed with dry Celite and filtered under a positive argon pressure. The solids were washed with 15 mL of diethyl ether and the cloudy filtrate was treated with 3.8 mL (40.0 mmol) of distilled ethyl chloroformate. After stirring for 18 hours at room temperature, the solvents were evaporated and the residue was partitioned between ethyl acetate and saturated $NaHCO_3$. The organic layer was washed with saturated $NaHCO_3$ and brine, dried ($MgSO_4$) and evaporated to provide 1.44 g of a pale yellow oil. Flash chromatography on 175 g of silica gel eluted with 25:75 ethyl acetate:petroleum ether gave 1.08 g (68%) of title compound as a colorless liquid.

TLC Silica gel (50:50 ethyl acetate:hexane) $R_f=0.41$.

IR(neat) 2965, 2927, 2873, 2858, 1715, 1448, 1386, 1248, 1200, 1032 cm$^{-1}$.

$^1$H NMR(CDCl$_3$, 270 MHz): δ 5.09 (br, 3H), 4.32 (t, 2H, J=7.5 Hz), 4.28 (m, 2H), 1.8–2.2 (m, 12H), 1.68 (s, 3H), 1.60 (s, 9H), 1.36 (m, 6H) ppm.

Mass Spec (CI-CH$_4$/N$_2$O, + ions) m/e 398 (M+H), 325, 285, 263.

EXAMPLE 2

(E,E)-[Hydroxy(5,9,13-trimethyl-4,8,12-tetradecatrienyl)phosphinyl]formic acid, disodium salt To a stirred solution of 574.4 mg (1.44 mmol) of Example 1 compound in 5 mL of dry dichoromethane at −18° C. under argon was added 0.19 mL (1.44 mmol) of 2,4,6-collidine followed by 0.41 mL (2.88 mmol) of iodotrimethylsilane. The reaction was allowed to stir for one hour at −18° C. and 1.5 hours at 0° C. An additional portion of iodotrimethylsilane (0.10 mL, 0.70 mmol) was added and after an additional 30 minutes at 0° C., the solvents were evaporated and the residue was pumped under vacuum. The residue was dissolved in 7.5 mL (7.5 mmol) of 1 M NaOH and the solution was stirred for two hours at room temperature followed by two hours at 65° C. The aqueous solution was lyophilized and the crude tan powder was chromatographed on a 2.5 cm diameter×20 cm height column of CHP20P packed in water. The column was eluted with water (fractions 1–5) followed by a gradient created by the addition of 600 mL of 70:30 acetonitrile:water to 600 mL of water, collecting approximately 10 mL fractions. Fractions 48–58 were combined and lyophilized to provide 374.7 mg (65%) of title compound as a white powder.

TLC Silica gel (7:2:1 n-C$_3$H$_7$OH:con NH$_3$:H$_2$O) $R_f=0.47$.

IR(KBr) 3433 (br), 2967, 2928, 2859, 1573, 1448, 1383, 1366, 1189, 1057 cm$^{-1}$.

$^1$H NMR(D$_2$O, 400 MHz): δ 5.17 (t, 1H, J=7 Hz), 5.07 (m, 2H), 1.9–2.1 (m, 10H), 1.60 (s, 3H), 1.57 (s, 3H), 1.53 (s, 3H), 1.52 (s, 3H), 1.47 (m, 3H) ppm.

$^{31}$P NMR (D$_2$O, 109 MHz): δ 27.95 (singlet) ppm.

Mass Spec (FAB, + ions) m/e 425 (M+2Na-H), 409 (M+Na), 387 (M+H).

Anal. Calc'd for C$_{18}$H$_{29}$PO$_4$Na$_2$ (MW 386.42): C, 55.94; H, 7.58; P, 8.02.

Found*: C, 56.00; H, 7.49; P, 8.27.

*Sample was dried at 50° C. under vacuum prior to analysis.

EXAMPLE 3

(E,E)-[Hydroxy(5,9,13-trimethyl-4,8,12-tetradecatrienyl)phosphinyl]formic acid, ethyl ester, monopotassium salt To a stirred solution of 498.5 mg (1.25 mmol) of Example 1 compound in 3 mL of dry dichloromethane at 0° C. under argon was added 0.17 mL (1.29 mmol) of 2,4,6-collidine followed by 0.36 mL (2.50 mmol) of iodotrimethylsilane, dropwise over 2 minutes. The colorless solution was allowed to stir at 0° C. for 1.7 hours, the solvent was evaporated and the residue was pumped at high vacuum for 30 minutes. The oil was treated with 0.26 mL (1.86 mmol) of triethylamine in 2 mL of water for 10 minutes, and the mixture was partitioned between dichloromethane and 1 M HCl. The aqueous layer was reextracted with dichloromethane, and the combined organic layers were washed with brine, dried (MgSO$_4$) and evaporated to provide 481 mg of a colorless oil. The crude acid was dissolved in 3 mL of methanol and treated with 1.25 mL of 1 M KOH to give a solution with a pH of 11. The methanol was evaporated and the aqueous solution was applied to a 20 cm long, 2.5 cm diameter column of CHP20P packed in water and eluted with a gradient created by the gradual addition of 600 mL of acetonitrile to 600 mL of water, collecting 8 mL fractions. Fractions 43–47 were combined, the acetonitrile evaporated and the aqueous solution freeze-dried. The residue was further dried at high vacuum to provide 274.4 mg (54%) of title compound as a dense, white lyophilate.

TLC Silica gel (7:2:1 n-C$_3$H$_7$OH:con NH$_3$:H$_2$O) $R_f=0.60$ or (8:1:1 CH$_2$Cl$_2$ CH$_3$OH:CH$_3$CO$_2$H) $R_f=0.30$.

IR (KBr) 2970, 2924, 2850, 1690, 1450, 1384, 1211, 1072 cm$^{-1}$.

$^1$H NMR (1:1 CD$_3$OD:D$_2$O, 400 MHz): δ 5.10 (t, 1H, J=7 Hz), 5.06 (t, 1H, J=7 Hz), 5.04 (t, 1H, J=7 Hz), 4.19 (q, 2H, J=7 Hz), 2.02, 1.94 (two m, 10 H), 1.69 (m, 2H), 1.61 (s, 3H), 1.57 (s, 3H), 1.54 (s, 6H) ppm.

Mass spec (FAB,+ions) m/e 447 (M+K), 409 (M+H).

Anal. Calc'd for C$_{20}$H$_{34}$O$_4$P$_2$K: C, 58.80; H, 8.39; P, 7.58 Found*: C, 59.91; H, 8.67; P, 7.64.

*Samples were dried at 50° C. under vacuum for 24 hours prior to analysis.

EXAMPLE 4

(E,E)-[Hydroxy[(5,9,13-trimethyl-4,8,12-tetradecatrienyl)oxy]phosphinyl]formic acid, disodium salt To a solution of 687 mg (3.6 mmol, 3 eq.) of (ethoxycarbonyl)phosphonic dichloride (preparation as described in Vaghefi, M. M.; McKernan, P. A.; and Robins, R. K.; *J. Med. Chem.*, (1986), 29, 1389) in 6 mL of dry tetrahydrofuran (THF) at −30° C. (CCl$_4$—CO$_2$) under argon was added dropwise a solution of 301 mg (1.2 mmol) of Example 1 Part A bishomofarnesol in 2 mL of dry THF over 5 minutes. After stirring for 1.5 hours, the -30° bath was replaced with a 0° C. bath and the reaction was immediately quenched with 9.6 mL (19.2 mmol, 16 eq.) of 2M NaOH. The mixture was stirred for two hours at room temperature, the THF was evaporated, and the aqueous mixture remaining was lyophilized. Purification was carried out by chromatography on a 2.5 cm diameter×18 cm height column of CHP20P packed in water. The crude compound was loaded as a suspension in 5 mL of water. The column was eluted with 200 mL of water, then 600 mL of 30:70 CH$_3$CN:H$_2$O, collecting 8-10 mL fractions every 1.5 minutes. Fractions 36-41 were combined, evaporated, lyophilized, and pump-dried overnight to obtain 214.1 mg (53%) of title compound as a white lyophilate.

TLC Silica gel (7:2:1 n-C$_3$H$_7$OH:NH$_3$:H$_2$O) R$_f$=0.47.

IR(KBr) 3500, 2964, 2925, 2890, 2856, 1581, 1447, 1373, 1227, 1091, 1051, 852, 619, 586 cm$^{-1}$.

$^1$H NMR (D$_2$O, 400 MHz): δ 5.19 (t, 1H, J=6.6 Hz), 5.11 (m, 2H), 3.87 (dt, 2H, J$_{HH}$=6.6, J$_{HP}$=7.0 Hz), 1.9-2.1 (m, 10H), 1.67 (m, 2H), 1.64 (s, 3H), 1.62 (s, 3H), 1.57 (s, 6H) ppm.

Mass Spec (FAB,+ions) m/e 425 (M+Na$^+$), 403 (M+H), 397 (M+2H-CO$_2$+K$^+$), 381 (M+2H-Na), 359 (M+H-CO$_2$).

Anal. Calc'd for C$_{18}$H$_{29}$O$_5$P.Na$_2$: C, 53.73; H, 7.26; P, 7.70 Found: C, 53.91; H, 6.81; P, 7.82.

The analytical sample was pig-dried at 50° C. for six hours.

EXAMPLE 5

(E,E)-[Ethoxy[[(3,7,11-trimethyl-2,6,10-dodecatrienyl)oxy]methyl]phosphinyl]formic acid, ethyl ester A. Tributyl[[(3,7,11-trimethyl-2,6,10-dodecatrienyl)oxy]methyl]tin A 1.15 g (10.0 mmol) of 35% KH in mineral oil was washed with three 5 mL portions of dry hexane and suspended in 15 mL of dry tetrahydrofuran (THF) under argon. A solution of 242 mg (0.95 mmol) of iodine in 10 mL of THF was added over 50 minutes and the reaction was allowed to stir for an additional 40 minutes at room temperature to give a white suspension. (E,E)-Farnesol (1.5 g, 6.75 mmol) in 10 mL of THF was added dropwise over 15 minutes, and after 75 minutes, a solution of 2.43 g (5.64 mmol) of tributyl(iodomethyl)tin was added rapidly in 6 mL of THF. The mixture was stirred for three hours and carefully quenched with methanol. Upon dilution with diethyl ether, the organic layer was washed with water and brine, dried (MgSO$_4$) and evaporated to give 3.21 g of a pale yellow liquid. The crude material was chromatographed on 720 g of silica gel eluted with 0.5:99.5 diethyl ether: petroleum ether, and the impure fractions were further purified on 150 g of silica gel eluted with 0.33:99.67 diethyl ether:petroleum ether to provide a total of 2.09 g (71%) of pure title stannane as a colorless liquid.

TLC Silica gel (2:98 diethyl ether:hexane) R$_f$=0.4.

IR(CCl$_4$) 2958, 2926, 2872, 2854, 1464, 1456, 1377, 1053 cm$^{-1}$.

$^1$H NMR(CDCl$_3$, 270 MHz): δ 5.32 (t, 1H, J=6.5 Hz), 5.12 (t, 1H, J=7.0 Hz), 5.09 (t, 1H, J=7.0 Hz), 3.87 (d, 2H, J=6.5 Hz), 3.72 (s, 2H), 2.05 (m, 8H), 1.68 (s, 3H), 1.66 (s, 3H), 1.60 (s, 6H), 1.52 (quint, 6H, J=8.0 Hz), 1.30 (sextet, 6H, J=8.0 Hz), 0.90 (m, 15H) ppm.

B. (E,E)-[Ethoxy[[(3,7,11-trimethyl-2,6,10-dodecatrienyl)oxy]methyl]phosphinyl]formic acid, ethyl ester To a solution of 855.8 mg (1.63 mmol) of Part C stannane in 11 mL of dry diethyl ether at −78° C. under argon was added in 1.12 mL (1.80 mmol) of n-butyllithium (1.6M in hexane) over 5 minutes. After 30 minutes at -78° C., 0.80 mL (5.53 mmol) of diethyl chlorophosphite was added as rapidly as possible. The cold bath was allowed to warm to room temperature very gradually over 3.5 hours, and the white suspension was allowed to stir for an additional 30 minutes at room temperature. Freshly distilled ethyl chloroformate (2.4 mL, 25.1 mmol) was added and the mixture was allowed to stir at room temperature for 160 minutes. The volatiles were removed in vacuo and the residue was diluted with ethyl acetate, washed with water (three portions), saturated NaHCO$_3$ and brine, dried (MgSO$_4$) and evaporated to provide 1.28 g of a colorless liquid. The crude product was flash chromatographed on 150 g of silica gel packed in 8:92 acetone:hexane and eluted with 12:88 acetone: hexane to provide 418.2 mg (64%) of pure title compound as a colorless oil.

TLC Silica gel (20:80 acetone:hexane) R$_f$=0.24.

IR(CCl$_4$) 2965, 2930, 2865, 1719, 1445, 1383, 1264, 1239, 1199, 1095, 1032, 965 cm$^{-1}$.

$^1$H NMR(CDCl$_3$, 270 MHz) δ 5.30 (t, 1H, J=7.0 Hz), 5.08 (m, 2H), 4.34 (q on m, 4H, Jq=6.0 Hz), 4.14 (d, 2H, J=7.0 Hz), 3.95 (ABX, 2H, J$_{AB}$=14 Hz, J$_{AX}$=7.0 Hz, J$_{BX}$=5.8 Hz), 2.08 (s, 8H), 1.68 (s, 6H), 1.60 (s, 6H), 1.40 (t, 3H, J=7.0 Hz), 1.36 (t, 3H, J=7.0 Hz) ppm.

Mass Spec (CI-CH$_4$/N$_2$O, +ions) m/e 401 (M+H), 429 (M+C$_2$H$_5$), 441 (M+C$_3$H$_5$).

EXAMPLE 6

(E,E)-[Hydroxy[[(3,7,11-trimethyl-2,6,10-dodecatrienyl)oxy]methyl]phosphinyl]formic acid, disodium salt A 490.4 mg (1.22 mmol) sample of Example 5 diester was stirred with 12 mL of 1M NaOH and 8 mL of distilled water for 1.5 hours at room temperature followed by 2.5 hours at 70° C. to give a homogeneous solution. Lyophilization gave a dense residue which was difficult to redissolve in water. The residue was heated to 90° C. in 10 mL of distilled water for 1 hour resulting in a homogeneous solution, which upon cooling to room temperature deposited a small amount of insoluble material. This solution was loaded onto a 2.5 cm diameter, 20 cm height column of CHP20P packed in water. The column was eluted with water (fractions 1-13), followed by a gradient created by the addition of 80:20 acetonitrile:water to a reservoir of 500 mL of water, such as to maintain the reservoir level at 500 mL (fractions 14-42). The addition of the acetonitrile mixture was discontinued after fraction 42 and the elution was continued isocratically. Approximately 10 mL fractions were collected. Fractions 38-50 were combined, the acetonitrile was evaporated and the aqueous remainder was freeze-dried to provide 337.3 mg (71%) of pure title compound as a fluffy-white lyophilate. The lyophilate was dried further at room temperature under high vacuum overnight. (Fractions 51-58 were similarly processed to provide 122 mg (25%) of slightly impure title compound.

TLC Silica gel (7:2:1 n-C$_3$H$_7$OH:con NH$_3$:H$_2$O) R$_f$=0.48.

IR(KBr) 3430, 2967, 2924, 2857, 1597, 1449, 1385, 1362, 1189, 1042, 764 cm$^{-1}$.

$^1$H NMR(D 0, 400 MHz) δ 5.37 (t, 1H, J=7.0 Hz), 5.15 (t, 1H, J=6.5 Hz), 5.12 (t, 1H, J=7.0 Hz), 4.11 (d, 2H, J=7.0 Hz), 3.70 (d, 2H, J=6.5 Hz), 2.10 (m, 6H), 1.98 (t, 2H, J=7.0 Hz), 1.69 (s, 3H), 1.65 (s, 3H), 1.59 (s, 3H), 1.58 (s, 3H) ppm.

Mass Spec (FAB, +ions) m/e 411 (M+Na), 367 (M+Na-CO$_2$), 345 (M+H-CO$_2$)

Anal. Calc'd for C$_{17}$H$_{27}$PNa$_2$O$_5$: C, 52.58; H, 7.01; P, 7.98 Found: C, 52.51; H, 7.27; P, 8.28.

EXAMPLE 7

(E,E)-[Ethoxy(6,10,14-trimethyl-5,9,13-pentadeca-trienyl)phosphinyl]formic acid, ethyl ester

A. 6,10,14-Trimethyl-5,9,13-pentadecatrien-1-ol

(1) 1-Chloro-3,7,11-trimethyl-2,6,10-dodecatriene (Note all temperatures indicated are for the contents of the reaction flask). To a stirred solution of 299 mg (2.24 mmol) of N-chlorosuccinimide in 15 mL of dichloromethane at -30° C. under argon was added 0.18 mL (2.45 mmol) of distilled dimethyl sulfide over 5 minutes. After 10 minutes at −30° C., the reaction was allowed to warm to 0° C. for 10 minutes, followed by cooling to −40° C. A solution of 441.4 mg (1.99 mmol) of 3,7,11-trimethyl-2,6,10-tridecatrien-1-ol in 5 mL of dichloromethane was added dropwise over 10 minutes. The reaction was allowed to warm gradually to 0° C. over 1 hour, and then maintained at 0° C. for 1 hour. After quenching with cold water, the mixture was extracted with hexane and the hexane extract was washed with cold water and cold brine, dried (MgSO4) and evaporated to afford 483 mg of a crude product. Rapid flash chromatography on 20 g of Merck 9385 silica gel eluted with 3:97 ethyl acetate:petroleum ether provided 406.5 mg (85%) of a colorless liquid. $^{13}C$ NMR indicated that this material contained a trace (3%) impurity.

TLC:Silica gel (2:98 ethyl acetate:hexane) $R_f=0.56$.

$^1H$ NMR(CDCl$_3$, 270 MHz): δ 5.44 (t, 1, J=7.9 Hz), 5.09 (t, 2, J=5.8 Hz), 4.07 (d, 2, J=7.9 Hz), 1.9–2.2 (m, 9), 1.72 (s, 3), 1.68 (s, 3), 1.60 (s, 6) ppm.

(2) Dichloro[mu-[1-propanolato(2-)-C$^3$:O$^1$]]dimagnesium

A modification of the procedure of G. Cahiez et al was employed (Tetrahedron Letters, 1978, 3013-4): To a stirred solution of 1.89 g (20 mmol) of 3-chloropropanol in 20 mL of THF under argon at −20° C. was added 10 mL (20 mmol) of 2M phenylmagnesium chloride in THF over 15 minutes. After 10 minutes at −20° C., the reaction was allowed to warm to room temperature, 730 mg (30 mmol) of magnesium turnings were added and the reaction was heated to reflux. Two 40 μL portions of 1,2-dibromoethane were added, the first portion injected at the start of reflux, and the second after 1 hour. After refluxing for a total of 2 hours, the reaction was allowed to cool to room temperature and was diluted with 37 mL of THF for a theoretical concentration of 0.3M.

(3) 6,10,14-Trimethyl-5,9,13-pentadecatrien-1-ol

A solution of 37.5 mL (20.3 mmol, 5.1 eq.) of a 0.54M solution of Grignard reagent (Part (2)) in tetrahydrofuran and 9 mL of hexamethylphosphoramide at room temperature under argon was treated over 10 minutes with a solution of 955.5 mg (3.97 mmol) of farnesyl chloride (Part (1)) in 5 mL of tetrahydrofuran. After one hour, the reaction mixture was diluted with a mixture of 1:1 diethyl ether:hexane and quenched with 1M HCl. The organic phase was washed with three 25 mL portions of saturated NaHCO$_3$, three 25 mL portions of H$_2$O, and 25 mL of brine, dried over MgSO$_4$ and evaporated to obtain 995.0 mg of crude product. Purification required two chromatographies. The first was run on 70 g of silica gel, eluting with 1:99 ethyl acetate:CH$_2$Cl$_2$ to provide 484.3 mg of impure material and 307.7 mg of pure title compound. The second chromatography, of the impure fractions, on 50 g of silica gel eluted with 0.75:99.25 ethyl acetate:CH$_2$Cl$_2$ gave 117.2 mg of slightly impure material and 302.8 mg of pure title compound. Combination of pure material from both columns gave a yield of 610.5 mg (58%) of pure desired title isomer.

TLC:Silica gel (10:90 diethyl ether:CH$_2$) $R_f=0.38$.

IR (CCL$_4$) 3639, 3450, 2964, 2930, 2858, 1449, 1382, 1058, 1028, 776, 750 cm$^{-1}$.

$^1H$ NMR(CDCl$_3$, 270 MHz): δ 5.10 (m, 3H), 3.62 (t, 2H, J=6.5 Hz), 2.00 (m, 10H), 1.69 (s, 3H), 1.61 (s, 9H), 1.2–1.7 (m, 5H, OH) ppm.

Mass Spec (CI-CH$_4$/N$_2$O, +ions) m/e 282 (M+NH$_4$), 265 (M+H), 263 (M+H-H$_2$).

B. (E,E)-15-Iodo-2,6,10-trimethyl-2,6,10-pentadecatriene

To a stirred solution of 363.8 mg (1.38 mmol) of Part A alcohol in 6 mL of dichloromethane at 0° C. was added 0.39 mL (2.76 mmol) of triethylamine followed by the dropwise addition of 0.14 mL (2.76 mmol) of methanesulfonyl chloride over 5 minutes. After stirring for 1 hour at 0° C., the mixture was diluted with diethyl ether and the organic phase was washed with 10% HCl, water, saturated NaHCO$_3$ and brine, dried (MgSO$_4$) and evaporated to give 458.8 mg of the mesylate as a colorless oil.

The crude mesylate was dissolved in 10 mL of acetone, treated with 414 mg (2.76 mmol) of sodium iodide and heated to 40° C. under argon for 17 hours. The mixture was diluted with hexane, washed with water, 4% sodium thiosulfate, water and brine, dried (MgSO$_4$), and evaporated to provide a colorless oil. Flash chromatography on 30 g of silica gel eluted with hexane gave 466.6 mg (90%) of the pure title iodide as a colorless oil.

TLC Silica gel (hexane) $R_f=0.32$.

IR (CCl$_4$) 2965, 2927, 2854, 1449, 1381, 1222, 809 cm$^{-1}$.

$^1H$ NMR(CDCl$_3$, 270 MHz): δ 5.10 (m, 3H), 3.18 (t, 2H, J=7 Hz), 2.00 (m, 10H), 1.82 (quint, 2H, J=7 Hz), 1.68 (s, 3H), 1.60 (s, 9H), 1.44 (m, 2H) ppm.

Mass Spec (CI-CH$_4$/N$_2$O, +ions) m/e 392 (M+NH$_4$), 375 (M+H).

C. (E,E)-[Ethoxy(6,10,14-trimethyl-5,9,13-pentadeca-trienyl)phosphinyl]formic acid, ethyl ester A solution of 266.4 mg (0.712 mmol) of the Part B iodide in 4 mL of diethyl ether was added dropwise over 20 minutes to a solution of 1 mL (1.7 mmol) of 1.7M t-butyllithium in pentane in 3 mL of diethyl ether at −78° C. under argon. After 45 minutes at −78° C., the solution was allowed to warm gradually to room temperature and stir for 1 hour. The anion was transferred via cannula with the aid of 2 mL of diethyl ether to the addition funnel of a second apparatus. This solution was added dropwise over 50 minutes to a solution of 0.23 mL (1.58 mmol) of diethyl chlorophosphite in 4 mL of diethyl ether at −78° C. After 50 minutes at −78° C., the reaction was allowed to warm gradually to room temperature over 2 hours and then stir at room temperature for 1 hour. Excess distilled ethyl chloroformate (0.7 mL, 7.32 mmol) was added, and the reaction was allowed to stir at room temperature for 16 hours. The white suspension was evaporated and the residue was dissolved in ethyl acetate, washed with saturated NaHCO$_3$, water and brine, dried (MgSO$_4$) and evaporated to provide 351 mg of a crude oil. The crude product was flash chromatographed on 40 g of silica gel eluted with 20:80 ethyl acetate:hexane to provide 169 mg (58%) of pure title compound as a colorless oil.

TLC Silica gel (50:50 ethyl acetate:hexane) $R_f=0.33$.
IR(CCl$_4$) 2979, 2928, 2856, 1712, 1445, 1251, 1196, 1032, 960 cm$^{-1}$.
$^1$H NMR(CDCl$_3$, 270 MHz): δ 5.03 (m, 3H), 4.25 (q, 2H, J=7.5 Hz), 4.20 (m, 2H), 1.93 (m, 12H), 1.62 (s, 3H), 1.52 (s, 9H), 1.49-1.61 (m, 2H), 1.38 (quint, 2H, J=7.5 Hz), 1.43, 1.44 (two t, 6H, J=7.5 Hz) ppm.
Mass Spec (CI-CH$_4$/N$_2$O, +ions) m/e 453 (M+C$_3$H$_5$), 441 (M+CH$_2$H$_5$), 413 (M+H).

EXAMPLE 8

(E,E)-[Hydroxy(6,10,14-trimethyl-5,9,13-pentadecatrienyl)phosphinyl]formic acid, disodium salt

To a stirred solution of 163.8 mg (0.397 mmol) of Example 7 ester in 2 mL of dry dichloromethane at 0° C. under argon was added 60 μL (0.45 mmol) of 2,4,6-collidine followed by 120 μL (0.843 mmol) of iodotrimethylsilane. After 1.5 hours at 0° C., the solution was evaporated, the residue was evaporated with benzene and pumped at high vacuum. This material was dissolved in 2.5 mL of 1M NaOH and stirred for 3 hours at room temperature followed by 2 hours at 65° C. The solution was lyophilized and the crude product was purified by MPLC on a 19 cm height, 2.5 cm diameter column of CHP20P. The column was packed and eluted with water (fractions 1-6), followed by a gradient created by the gradual addition of 75:25 acetonitrile:water to a reservoir of water, maintaining the reservoir volume at 500 mL. Fractions 31-38 were combined, the acetonitrile was evaporated and the residue was freeze-dried to give 84.4 mg (53%) of pure title product as a white lyophilate, which was dried further at high vacuum overnight.

TLC Silica gel (7:2:1 n-C$_3$H$_7$OH:con NH$_3$:H$_2$O) $R_f=0.41$
IR(KBr) 3450, 2966, 2927, 2857, 1574, 1448, 1382, 1365, 1184, 1112, 1054 cm$^{-1}$.
$^1$H MR(D$_2$O, 400 MHz): δ 5.18 (t, 1H, J=7 Hz), 5.12 (t, 1H, J=7 Hz), 5.10 (t, 1H, J=8 Hz), 2.04 (m, 10H), 1.64 (s, 3H), 1.60 (s, 3H), 1.56 (s, 6H), 1.5-1.7 (m, 2H), 1.49 (m, 2H), 1.37 (quint, 2H, J=7 Hz) ppm.
Mass Spec (FAB+ions) m/e 423 (M+Na), 401 (M+H), 379 (M+2H-Na), 357 (M+H-CO$_2$), 335 (M+2H-Na-CO$_2$).
Anal. Calc'd for C$_{19}$H$_{31}$PNa$_2$O$_4$.0.38 eq H$_2$O: C, 56.04; H, 7.86; P, 7.61 Found: C, 56.04; H, 7.87; P, 7.67.
*Analytical sample was weighed in a dry box into capsules.

EXAMPLE 9

(E,E)-[Hydroxy[(4,8,12-trimethyl-3,7,11-tridecatrienyl)oxy]phosphinyl]formic acid, disodium salt

A. (E,E)-4,8,12-Trimethyl-3,7,11-tridecatrien-1-ol (1) (E,E)-3,7,11-Trimethyl-2,6,10-dodecatrienaldehyde [(E,E)-Farnesal]

A solution of oxalyl chloride (4.68 g, 0.037 mol) in dry CH$_2$Cl$_2$ under argon atmosphere was cooled to −65° C. A solution of dimethyl sulfoxide (DMSO) (5.33 ml) in CH$_2$Cl$_2$ (17 ml) was added rapidly, dropwise, to the cooled oxalyl chloride solution. After stirring for 7 minutes at −65° C., a 10 ml CH$_2$Cl$_2$ solution of (E,E)-farnesol (7.0 g, 0.032 mol) was added over 10 minutes to the reaction solution at −65° C.: a precipitate formed upon the addition of approximately half of the farnesol solution. After the addition of the farnesol solution was completed, the reaction was stirred at −65° C. for 25 minutes, and then 22.4 ml (2 mol) of triethylamine was added over 10 minutes. After stirring for an additional 15 minutes at −65° C., the reaction was warmed to room temperature, and then diluted with water (∼200 ml). The resulting aqueous layer was extracted several times with CH$_2$Cl$_2$. The combined organic layers were washed once with saturated aqueous NaCl solution, once with 1% HCl, once with 5% Na$_2$CO$_3$ solution and once with saturated aqueous NaCl solution. The resulting organic layer was dried over MgSO$_4$ to give 7.05 g (100%) of a clear oil after filtration and solvent removal.

TLC Silica gel (20% ethyl acetate/hexane) $R_f=0.34$.
$^1$H NMR (CDCl$_3$, 270 MHz) 69.98 (d, 1H, J=7 Hz), 5.88 (broad d, 1H, J=7 Hz), 5.08 (m, 2H), 2.22 (m, 4H), 2.17 (s, 3H), 2.02 (m, 4H), 1.66 (s, 3H), 1.60 (s, 6H) ppm.
$^{13}$C-NMR (CDCl$_3$, 67.8 MHz) 6 191.0, 163.6, 136.5, 131.3, 127.4, 124.0, 122.4, 40.5, 39.6, 26.6, 25.6, 17.6, 17.5, 15.9 ppm.

(2) 4,8,12-Trimethyl-1,3,7,11-tridecatetraene

A suspension of methyltriphenylphosphonium iodide (8.07 g, 0.02 mole) in 61 ml of dry tetrahydrofuran (THF), under argon atmosphere was cooled to 0° C. To this suspension at 0° C. was added 9 mL (18 mmol) of phenyllithium (2.0M in diethyl ether/hexane 30:70) over 10 minutes. After the addition was complete, the reaction mixture containing excess phosphonium salt was warmed to room temperature and stirred for 40 minutes. The reaction mixture was then recooled to 0° C., and a 10 ml THF solution of the Part (1) aldehyde (4.0 g, 0.018 mol) was added over 12 minutes. After stirring for 10 minutes at 0° C., the reaction was warmed to room temperature. The reaction was quenched with CH$_3$OH after 2 hours at room temperature. The THF was removed from the reaction mixture to give a slurry which was triturated with petroleum ether, and subsequently, filtered through a Celite pad in a sintered glass funnel. The solids were then boiled in petroleum ether and refiltered as above. The resulting yellow oil was passed through 50 g of Florisil (100–200 mesh) eluted with ∼400 ml of petroleum ether providing the title tetraene (3.36 g, 86%) as a clear oil after solvent removal.

TLC Silica gel (20% ethyl acetate/hexane) $R_f=0.68$.
$^1$H NMR (CDCl$_3$, 270 MHz) δ 6.56 (ddd, 1H, J=17, 12, 6 Hz), 5.85 (d, 1H, J=12 Hz), 5.10 (m, 2H), 5.02 (m, 2H), 2.05 (m, 8H), 1.75 (s, 3H), 1.67 (s, 3H), 1.60 (s, 6H) ppm.
$^{13}$C-NMR (CDCl$_3$, 67.8 MHz) δ 139.3, 135.3, 133.4, 131.2, 125.5, 124.3, 123.9, 114.5, 39.9, 39.7, 26.8, 26.4, 25.6, 17.7, 16.6, 15.9 ppm.

(3) (E,E)-4,8,12-Trimethyl-3,7,11-tridecatrien-1-ol

Neat 2-methyl-2-butene (2.25 g, 0.032 mol) was added to a 1.0M BH$_3$-THF solution (16.9 ml) at −50° C. and under argon. After the addition was complete, the reaction was stirred for 2 hours at 0° C. The resulting disiamylborane solution was transferred via cannula over 1 hour to a flask containing a 17 ml THF solution of Part A(2) tetraene (3.36 g, 0.015 mol) under argon atmosphere and cooled to 0° C. After the transfer was complete, the reaction was allowed to gradually warm to room temperature, and then it was stirred overnight at room temperature. The reaction mixture was cooled to 0° C., and 5.1 ml of 3N NaOH was added rapidly. After stirring for 10 minutes, the reaction mixture was cooled in an ice-salt bath and 5.1 ml of 30% $H_2O_2$ was added dropwise. Subsequently, the reaction was warmed to room temperature and stirred for 4 hours after which it was diluted with $H_2O$, and the resulting aqueous layer was extracted several times with diethyl ether. The combined organic layers were dried over $MgSO_4$. Purification by flash chromatography eluting with 20% ethyl acetate/hexane provided the title alcohol (2.62 g, 74%) as a clear oil.

TLC Silica gel (20% ethyl acetate/hexane) $R_f = 0.23$.

IR (Film) 3340 (br), 2965, 2920, 1665, 1440, 1380, 1100, 1050 cm$^{-1}$.

$^1$H NMR (CDCl$_3$, 270 MHz) δ 5.10 (m, 3H), 3.61 (t, 2H, J=6 Hz), 2.29 (q, 2H, J=6 Hz), 2.03 (m, 8H), 1.67 (s, 3H), 1.65 (s, 3H), 1.60 (s, 6H) ppm.

$^{13}$C NMR (CDCl$_3$, 67.8 MHz) δ 138.8, 135.2, 131.2, 124.3, 123.9, 119.9, 62.4, 39.8, 39.7, 31.5, 26.7, 26.5, 25.6, 17.6, 16.1, 15.9 ppm.

B.
(E,E)-[Hydroxy[(4,8,12-trimethyl-3,7,11-tridecatrienyl-)oxy]phosphinyl]formic acid, disodium salt To a solution of 967.5 mg (5.08 mmol, 3 eq.) of (ethoxycarbonyl)phosphonic dichloride (preparation as described in Vaghefi, M. M.; McKernan, P. A.; and Robins, R. K.: *J. Med. Chem.*, (1986), 29, 1389) in 10 mL of dry THF at −30° C. (CCl$_4$–CO$_2$) under argon was added dropwise a solution of 400.2 mg (1.7 mmol) of Part A homofarnesol in 4 mL of dry THF over 8 minutes. After stirring for two hours, the −30° C. bath was replaced with a 0° C. bath and the reaction was immediately quenched with 13.6 mL (27.2 mmol, 16 eq.) of 2 N NaOH. The mixture was stirred for three hours at room temperature, the THF was evaporated, and the aqueous mixture remaining was lyophilized. Purification was carried out by chromatography on a 2.5 cm diameter × 18 cm height column of CHP20P packed in water. The crude compound was loaded as a suspension in 6 mL of water. The column was eluted with 250 mL of water, then 600 mL of 30:70 CH$_3$CN:H$_2$O, collecting 8–10 mL fractions every 1.5 minutes. Fractions 40–44 were combined, the acetonitrile was evaporated, and the aqueous solution was lyophilized. The residue was pump-dried overnight to obtain 341.5 mg (52%) of a fluffy, white lyophilate.

TLC Silica gel (7:2:1 n-C$_3$H$_7$OH:NH$_3$:H$_2$O) $R_f = 0.38$.

IR(KBr) 3440, 2967, 2925, 2856, 1581, 1447, 1424, 1372, 1227, 1093, 1073, 1034, 847, 798, 774 cm$^{-1}$.

$^1$H NMR(D$_2$O, 400 MHz) δ 5.18 (t, 1H, J=6.6 Hz), 5.12 (m, 2H), 3.82 (q, 2H, J$_{HH}$=7.3 Hz, J$_{HP}$=7.3 Hz), 3.37 (dt, 2H, J=6.6, 7.3 Hz), 1.9–2.1 (m, 8H), 1.65 (s, 6H), 1.58 (s, 3H), 1.57 (s, 3H) ppm.

Mass Spec (FAB,+ions) m/e 411 (M+Na), 389 (M+H), 383 (M+2H+K-2Na), 367 (M+2H-Na), 345 (M+H-CO$_2$), 281.

Anal. Calc'd for C$_{17}$H$_{27}$O$_5$P.Na$_2$: C, 52.58; H, 7.01; P, 7.98 Found: C, 52.76, H, 6.92; P, 7.77.

The analytical sample was dried at 50° C. for six hours.

EXAMPLE 10

(E,E)-[Hydroxy[(4,8,12-trimethyl-3,7,11-tridecatrienyl-)oxy]phosphinyl]formic acid, ethyl ester, monosodium salt To a solution of 965.3 mg (5.08 mmol, 3 eq.) of (ethoxycarbonyl)phosphonic dichloride in 10 mL of dry THF at −30° C. (CCl$_4$–CO$_2$) under argon was added dropwise over seven minutes a solution of 397.1 mg (1.7 mmol) of Example 9, Part A homofarnesol in 4 mL of THF. After stirring for 2.5 hours at −30° C. the cold batch was removed, the reaction was immediately quenched with 2 mL of water and stirring continued for an additional one-half hour. The mixture was diluted with 40 mL of diethyl ether and washed with four 10 mL portions of water, and 10 mL of brine, dried over MgSO$_4$ and evaporated to obtain 640.9 mg of crude phosphonic acid. The crude acid was dissolved in 2 mL of 1:1 ethanol:H$_2$O and the solution was treated with 1.7 mL (1.7 mmol, leq.) of 1M NaOH to attain pH 6.15. The ethanol was evaporated and the remaining aqueous solution was lyophilized to obtain 571.0 mg of crude title compound. Purification was by chromatography on a 2.5 cm diameter × 18 cm height column of CHP20P packed in water and eluted with a gradient created by the gradual addition of 300 mL of CH$_3$CN into 300 mL of 5:95 CH$_3$CN:H$_2$O. Approximately 10 mL fractions were collected every 1.5 minutes. Fractions 34–39 were combined, evaporated, lyophilized and pump-dried overnight to obtain 315.1 mg (47%) of title compound as a gummy white lyophilate.

TLC Silica gel (7:2:1 n-C$_3$H$_7$OH:con NH$_3$:H$_2$O) $R_f = 0.68$.

IR(KBr) 2967, 2928, 2917, 2856, 1690, 1472, 1447, 1383, 1261, 1095, 1064, 1021, 940, 858, 792, 785, 768, 759 cm$^{-1}$.

$^1$H NMR(1:1 CD$_3$OD:D$_2$O, 400 MHz) δ 5.28 (t, 1H, J=7.0 Hz), 5.21 (m, 2H), 4.36 (q, 2H, J=7.0 Hz), 4.04 (q, 2H, J=7.0 Hz), 2.49 (q, 2H, J=7.0 Hz), 2.0–2.2 (m, 8H), 1.78 (s, 3H), 1.76 (s, 3H), 1.70 (s, 6H), 1.44 (dt, 3H, J=1.1, 7.0 Hz) ppm.

Mass Spec (FAB,+ions) m/e 433 (M+K), 417 (M+Na), 395 (M+H), 347.

Anal. Calc'd for C$_{19}$H$_{32}$O$_5$P.Na: C, 57.86; H, 8.18; P, 7.85 Found: C, 58.37; H, 8.16; P, 7.65.

The analytical sample was dried at 50° C. for six hours.

EXAMPLE 11A (E,E)-[Ethoxy(4,8,12-trimethyl-3,7,11-tridecatrienyl)-phosphinyl]formic acid, ethyl ester A. (E,E)-3,7,11-Trimethyl-2,6,10-dodecatrienyl bromide A solution of 1.00 g (4.5 mmol) of (E,E)-farnesol in 10 mL of distilled diethyl ether at 0° C. under argon in the dark was treated dropwise with a solution of 195 μL (2.05 mmol, 0.45 eq.) of PBr$_3$ in 2 mL of diethyl ether. The resultant mixture ws stirred at 0° C. for one hour, then quenched with water and separated. The organic phase was washed with 5 mL of H$_2$O, 5 mL of saturated NaHCO$_3$, and 5 mL of brine, dried over Na$_2$SO$_4$ and evaporated to give 1.26 (98%) of crude bromide as a clear oil.

TLC Silica (2:8 ethyl acetate:hexane) $R_f = 0.69$ (decomposes).

¹H NMR (CDCl₃) δ 5.52 (t, 1H, J=8.5 Hz), 5.08 (m, 2H), 4.01 (d, 2H), 1.9-2.2 (m, 8H), 1.73 (s, 3H), 1.68 (s, 3H), 1.60 (s, 6H) ppm.

B.
(E,E)-4,5-Dihydro-2-[(3,7,11-trimethyl-4,8,12-tridecatrienyl)thio]thiazole To a stirred solution of 3.57 g (26.8 mmol) of 1-methylthio(thiazoline) in 50 mL of THF at −78° C. under argon was added 16 mL (25.6 mmol) of 1.6M n-butyllithium in hexane over 15 minutes to give a yellow solution. After stirring for one hour, 6.33 g (22.4 mmol) of Part A bromide in 10 mL of THF was added over 15 minutes. The reaction was allowed to stir for one hour at −78° C., warm gradually to 0° C. for one hour, stir at 0° C. for one hour followed by quenching with saturated NH₄Cl. The mixture was extracted with diethyl ether, washed with water and brine, dried (MgSO₄) and evaporated to provide 9 g of a crude yellow liquid. This material was flash chromatographed on 500 g of silica gel, packed in 1.5:98.5 THF/petroleum ether and eluted with 3:97 THF/petroleum ether to afford 6.49 g (85%) of pure title compound as a colorless liquid.

TLC Silica gel (10:90 ethyl acetate/hexanes) $R_f$=0.29.

IR (CCl₄) 2965, 2923, 2852, 1570, 1446, 1382, 1304, 1280, 1108, 1097, 1071, 1018, 996, 920 cm⁻¹.

D.
(E,E)-[Ethoxy(4,8,12-trimethyl-3,7,11-tridecatrienyl)phosphinyl]formic acid, ethyl ester To a solution of 1.7 mL (2.74 mmol) of 1.6M t-butyllithium in pentane in 3 mL of diethyl ether at −78° C. under argon was added 482.4 mg (1.39 mmol) of the Part C iodide in 4 mL of diethyl ether over 10 minutes. After 45 minutes at −78° C., the pale yellow suspension was allowed to warm to 0° C. for one hour, and then transferred to an addition funnel of a second apparatus via cannula under argon. The lithium reagent solution was added dropwise over 45 minutes to 0.20 mL (1.39 mmol) of diethyl chlorophosphite in 4 mL of diethyl ether at 0° C. After 20 minutes at 0° C. and 1.5 hours at room temperature, the white suspension was cannulated into a Schlenck filter, and filtered through dry Celite. The solids were washed with 15 mL of diethyl ether, and the filtrate was treated with 1.3 mL (13.6 mmol) of distilled ethyl chloroformate. The mixture was allowed to stir for 21 hours at room temperature, the solvents were evaporated and the residue was partitioned between ethyl acetate and saturated NaHCO₃. The organic layer was washed with saturated NaHCO₃ and brine, dried (MgSO₄), and evaporated to provide 490.6 mg of a pale yellow oil. Flash chromatography on 45 g of silica gel packed in 10% THF/hexane and eluted with 20-30% THF/hexane gave 192.5 mg (36%) of title ester as a colorless oil.

TLC Silica gel (30:70 THF/hexane) $R_f$=0.30.

¹H NMR (CDCl₃) δ 5.10 (m, 3H), 4.20 (t, 2H, J=7.9 Hz), 3.36 (t, 2H, J=7.9 Hz), 3.09 (t, 2H, J=7.4 Hz), 2.39 (q, 2H, J=7.4Hz), 2.00 (m, 8H), 1.68 (s, 3H), 1.62 (s, 3H), 1.60 (s, 6H) ppm.

C. (E,E)-13-Iodo-2,6,10-trimethyl-2,6,10-tridecatriene 2.98 g (8.83 mmol) of Part B compound in 6 mL of dimethylformamide (DMF) in a pressure bottle was treated with 42 mg of calcium carbonate and two drops of mercury, and then flushed with argon. Iodomethane (12 mL, 193 mmol) was added, the bottle sealed and the contents heated at 60°-70° C. for 22 hours. The mixture was diluted with an equal volume of petroleum ether and the salts were removed by filtration. The volatiles were removed by short-path distillation at 60° C. at atmospheric pressure followed by aspirator pressure. The yellow residue was dissolved in 100 mL of hexane and washed with 2% Na₂S₂O₃ (2×25 mL), water (2×25 mL), and brine, dried (MgSO₄) and evaporated to provide 2.95 g of a crude yellow liquid. The crude material was flash chromatographed on 225 g of silica gel eluted with petroleum ether to provide 2.506 g (82%) of title iodide as a colorless oil.

TLC Silica gel (hexane) $R_f$=0.33.

¹H NMR (CDCl₃) δ 5.11 (m, 3H), 3.10 (t, 2H, J=7 Hz), 2.58 (q, 2H, J=7 Hz), 2.00 (m, 8H), 1.68 (s, 3H), 1.60 (s, 9H) ppm.

IR (CCl₄) 2981, 2927, 2915, 1714, 1445, 1252, 1195, 1164, 1034, 961, 859, 801 cm⁻¹.

¹H NMR (CDCl₃) δ 5.10 (m, 3H), 4.30 (m, 4H), 2.34 (m, 2H), 2.00 (m, 10H), 1.68 (s, 3H), 1.63 (s, 3H), 1.60 (s, 6H), 1.36 (m, 6H) ppm.

Mass Spec (CI-CH₄/N₂O,+ions) m/e 413 (M+C₂H₅), 385 (M+H).

EXAMPLE 11B
(E,E)-[Hydroxy(4,8,12-trimethyl-3,7,11-tridecatrienyl)phosphinyl]formic acid, disodium salt To a stirred solution of 185.4 mg (0.482 mmol) of Example 11A ester in 3 mL of dry CH₂Cl₂ at 0° C. under argon was added 70 µL (0.53 mmol) of 2,4,6-collidine followed by 0.15 mL (1.05 mmol) of iodotrimethylsilane. The reaction was allowed to stir for 2.5 hours at 0° C. and then the volatiles were evaporated and the residue was pumped at high vacuum. To the remainder was added 2.5 mL of 1M NaOH, and the solution was stirred at room temperature for 1.5 hours followed by 80° C. for 2 hours. After freeze drying, the tan crude product was purified by MPLC on CHP20P gel (2.5 cm diameter, 15 cm height), eluted with a gradient created by the gradual addition of methanol to a reservoir of 10:90 water: methanol. The appropriate fractions were combined, the methanol evaporated, and the aqueous remainder was freeze-dried to provide 110 mg (61%) of pure title salt as a white lyophilate.

TLC Silica gel (7:2:1 n-propanol:con NH₃:water) $R_f$=0.49.

IR (KBr) 2967, 2924, 2856, 1574, 1447, 1182, 1053 cm⁻¹.

¹H NMR (D₂O, 400 MHz) δ 5.25 (t, 1H, J=7 Hz), 5.17 (m, 2H), 2.17 (m, 2H), 2.01 and 2.10 (two m, 4H each), 1.67 (s, 3H), 1.63 (s, 3H), 1.60 (s, 6H), 1.60-1.75 (m, 2H) ppm.

¹³C NMR (D₂O, 67.8 MHz) δ 180.9 (d, J=162.8 Hz), 136.5, 136.4, 133.0, 124.8, (d, J=9 Hz), 124.5, 39.1, 39.0, 29.38 (d, J=87 Hz), 26.0, 25.1, 20.7, 17.2, 15.5, 15.4 ppm.

Anal. Calc'd for C₁₇H₂₇O₄PNa₂: C, 54.83; H, 7.31; P, 8.32 Found: C, 55.01; H, 7.29; P, 8.48.

The analytical sample was dried to constant weight at 50° C.

EXAMPLE 12A (E,E)-(5,9,13-Trimethyl-4,8,12-tetradecatrienyl)phosphinic acid, ethyl ester

A.
(E,E)-14-Iodo-2,6,10-trimethyl-2,6,10-tetradecatriene

The crude Example 1, Part B mesylate prepared from 441.1 mg (1.76 mmol) of the corresponding alcohol according to the procedure of Example 1, Part B, was dissolved in 5 mL of acetone and treated with 530 mg (3.52 mmol) of sodium iodide. The reaction was allowed to stir for 16 hours at room temperature followed by 5 hours at reflux. The suspension was diluted with hexane and stirred with dilute aqueous sodium bisulfite to discharge the yellow color. The organic layer was washed with water and brine, dried (MgSO$_4$), and evaporated to provide 577 mg of crude product. Flash chromatography on 35 g of silica gel eluted with hexane gave 550.9 mg (87%) of title iodide as a colorless liquid.

TLC Silica gel (hexane) R$_f$=0.31.

$^1$H NMR (CDCl$_3$, 270 MHz) δ 5.09 (m, 3H), 3.16 (t, 2H, J=7.0 Hz), 1.8–2.2 (m, 12H), 1.67 (s, 3H), 1.63 (s, 3H), 1.59 (s, 6H) ppm.

Mass Spec (CI-CH$_4$/N$_2$O,+ions) m/e 361, 359 (M+H), 137.

B.
(E,E)-(5,9,13-Trimethyl-4,8,12-tetradecatrienyl)phosphinic acid, ethyl ester A solution of 632 mg (1.75 mmol) of Part A iodide in 5 mL of diethyl ether was added dropwise over 25 minutes to a solution of 2.20 mL (3.74 mmol) of t-butyllithium (1.7M in pentane) in 6 mL of diethyl ether under argon. After 30 minutes at −78° C. and 30 minutes at room temperature, the solution was cannulated into the addition funnel of a second apparatus with the aid of 2 mL of diethyl ether. This solution was added over 50 minutes to a stirred solution of 0.51 mL (3.5 mmol) of diethyl chlorophosphite in 5 mL of diethyl ether at −78° C. under argon. After 30 minutes at −78° C., the reaction was allowed to gradually warm to 0° C. over 50 minutes, maintained at 0° C. for one hour, and quenched with 5 mL of water which had been deaerated with a stream of nitrogen. After 75 minutes, the mixture was extracted with diethyl ether and the ether layer was washed with water (four portions) and brine, dried (MgSO$_4$), and evaporated to afford 560 mg of a colorless oil. The oil was subjected to flash chromatography on 70 g of SilicAR-CC7 silica gel packed in 50:50 ethyl acetate:petroleum ether, eluted with a 60:40 mixture (fractions 1–30), followed by neat ethyl acetate. Fractions 19–64 gave 446.5 mg (78%) of title compound as a colorless oil. The title compound may be used in forming compounds of the invention by following the procedures described hereinbefore or by reacting the Part B compound with ethyl chloroformate following the procedure described in Example 15, to form Example 1, Part D product.

TLC Silica gel (ethyl acetate) R$_f$=0.22.

IR (CCl$_4$) 2978, 2928, 2856, 2331, 1449, 1444, 1233, 1054, 956, 804, 751 cm$^{-1}$.

$^1$H NMR (CDCl$_3$, 270 MHz) δ 7.07 (d, 1H, J=5.26 Hz), 5.09 (m, 3H), 4.10 (m, 2H), 1.8–2.2 (m, 10H), 1.5–1.9 (s, 4H), 1.67 (s, 3H), 1.60 (s, 9H), 1.36 (t, 3H, J=7 Hz) ppm.

Mass Spec (CI-CH$_4$/H$_2$O) (+ions) m/e 653 (2M+H) (−ions) m/e 352 (M-H).

EXAMPLE 12B (E,E)-(5,9,13-Trimethyl-4,8,12-tetradecatrienyl)-phosphinic acid, potassium salt To a stirred solution of 446 mg (1.37 mmol) of Example 12A, Part B compound in 5 mL of methanol under argon was treated with 2.8 mL of 1M KOH. After stirring for 2 hours at room temperature, the methanol was evaporated and the residue was stirred with 40 mL of diethyl ether and 5 mL of 1M HCl. The ether layer was washed with water and brine, dried (MgSO$_4$) and evaporated to provide 391.2 mg (92%) of the free acid as a colorless liquid. The acid was purified as the ammonium salt: a solution of the acid in 12 mL of diethyl ether was treated in a centrifuge tube with 8 mL of ammonia saturated diethyl ether. After cooling to 0° C. and centrifuging, the pellet was washed twice with ice cold 2:1 diethyl ether:hexane. The resulting granular solid was dried under vacuum to provide an oily wax, indicative of counterion loss during drying. The residue was dissolved in 5 mL of 0.5M KOH and lyophilized. The residue was chromatographed on a 18 cm height, 2.5 cm diameter column of CHP20P eluted with water (fractions 1–20) followed by 50:50 acetonitrile:water (fractions 21–50) collecting 10–15 mL fractions. Fractions 29–35 were freeze-dried to give 350.6 mg (76%) of title compound as an off-white, dense, sticky lyophilate which was dried further at high vacuum. The title compound was mildly sensitive to air oxidation to the corresponding phosphonic acid, a trace of which was noted on TLC. The so-formed title compound may be employed to form compounds of the invention following the procedures described hereinbefore, as well as outlined in Example 17.

TLC Silica gel (8:1:1 n-C$_3$H$_7$OH:con NH$_3$:H$_2$O) R$_f$=0.42. Silica gel (8:1:1 CH$_2$Cl$_2$:CH$_3$OH:CH$_3$CO$_2$H) R$_f$=0.44.

IR (KBr) 3360, 2968, 2922, 2858, 2289, 1665, 1449, 1159, 1064 cm$^{-1}$.

$^1$H NMR (CD$_3$OD, 400 MHz) δ 6.97 (dt, 1H, J$_{P-H}$=486 Hz, J$_{H-H}$=2 Hz, P-H), 5.10 (m, 3H), 1.9–2.2 (m, 10H), 1.66 (s, 3H), 1.61 (s, 6H), 1.59 (s, 6H), 1.4–1.7 (m, 4H) ppm.

Mass Spec (FAB+ions) m/e 375 (M+K), 359 (M+Na), 337 (M+H).

Anal. Calc'd for C$_{17}$H$_{30}$KO$_2$P: C, 60.68; H, 8.99; P, 9.20 Found*: C, 60.70; H, 9.07; P, 8.80.
*Sample was dried at 50° C. for 6 hours.

EXAMPLE 13

(E,E)-[[(3,7,11-Trimethyl-2,6,10-dodecatrienyl)oxy]methyl]phosphinic acid, ethyl ester To a stirred solution of 1.302 g (2.48 mmol) of Example 5, Part A stannane in 12 mL of dry diethyl ether at −78° C. under argon was added 1.8 mL (2.88 mmol) of 1.6M n-butyllithium in hexane over 7 minutes. After 30 minutes at −78° C., 1.24 mL (8.64 mmol) of diethylchlorophosphite was added rapidly in one portion. The reaction was maintained at −78° C. for one hour, followed by gradual warming to room temperature over two hours. After stirring at room temperature for 50 minutes, the reaction was quenched with 2 mL of water (deoxygenated by nitrogen bubbling), stirred for 40 minutes and extracted with diethyl ether. The ether layer was washed with four portions of water, dried (MgSO$_4$), and evaporated to provide 1.65 g of a colorless liquid. The crude product was dissolved in 20 mL of acetonitrile and washed with two-10 mL portions of hexane. The acetonitrile layer was concentrated to give 546.2 mg (67%) of title phosphonous monoester. Integration of the $^1$H-NMR spectrum of the crude material suggested that it contained some free phosphonous acid. The title compound may be employed in preparing compounds of the invention employing procedures described hereinbefore, and was utilized in Example 15.

TLC Silica gel (Ethyl Acetate) $R_f$=0.37.

IR (CCl$_4$) 2970, 2926, 2917, 2857, 2380, 1667, 1448, 1383, 1191, 1108, 1091, 986, 836, 781 cm$^{-1}$.

$^1$H NMR (CDCl$_3$, 270 MHz) δ 7.14 (dt, 1H, J=551, 2 Hz), 5.30 (t, 1H, J=7 Hz), 5.09 (br m, 2H), 4.18 (m, 2H), 4.12 (d, 2H, J=7 Hz), 3.76 (m, 2H), 2.07 (m, 8H), 1.69, 1.68 (two s, 6H), 1.60 (s, 6H), 1.40 (t, 3H, J=7 Hz) ppm.

Mass Spec (CI-H$_2$O/CH$_4$,+ions) m/e 329 (M+H).

EXAMPLE 14

(E,E)-(4,8,12-Trimethyl-3,7,11-tridecatrienyl)phosphinic acid, ethyl ester

To a stirred solution of 3.6 mL (5.76 mmol) of 1.6M t-butyllithium in pentane in 8 mL of diethyl ether at −78° C. under argon was added 995 mg (2.87 mmol) of Example 11, Part C iodide in 4 mL of diethyl ether over 12 minutes to give a thin yellow suspension. After 50 minutes, the reaction was allowed to warm to 0° C. for 50 minutes. The anion solution was cannulated into the addition funnel of a second apparatus and was added dropwise over 50 minutes to 0.83 mL (5.73 mmol) of diethyl chlorophosphite in 8 mL of diethyl ether at −78° C. The resulting thin suspension was stirred for 1 hour at −78° C., allowed to warm to 0° C. over 1 hour, and then maintained at 0° C. for 1 hour. The suspension was filtered through dry Celite in a Schlenck filter under argon, and the solids were washed 2×15 mL of diethyl ether. The ether was distilled off under argon and the residue was treated with 10 mL of water containing three drops of concentrated HCl which had been deaerated by nitrogen bubbling. The mixture was stirred for 45 minutes at room temperature, some ethyl acetate was added and stirring was continued for 30 minutes. The mixture was extracted with ethyl acetate, washed with water (5 times), dried (MgSO$_4$) and evaporated to provide 842 mg of a colorless oil. The crude product was flash chromatographed on 70 g of silica gel eluted with 50:50 ethyl acetate:petroleum ether to provide 268.4 mg (30%) of a colorless oil which is useful in preparing compounds of the invention.

TLC Silica gel (75:25 ethyl acetate:hexane) $R_f$=0.28.

EXAMPLE 15

(E,E)-[Ethoxy[[(3,7,11-trimethyl-2,6,10-dodecatrienyl)oxy]methyl]phosphinyl]formic acid, ethyl ester To a stirred solution of 110.4 mg (0.336 mmol) of Example 13 ester in 2 mL of diethyl ether was added 64 μL (0.504 mmol) of chlorotrimethylsilane, 64 μL (0.672 mmol) of ethyl chloroformate and 70 μL (0.504 mmol) of triethylamine. The reaction was allowed to stir for 5 hours at room temperature, diluted with diethyl ether, washed with 1M HCl, water and brine, dried (MgSO$_4$) and evaporated to provide 117 mg of title ester as a colorless oil, contaminated with the corresponding phosphinic monoacid.

TLC Silica gel (ethyl acetate) R =0.57.

EXAMPLE 16

(E,E)-[[(3,7,11-Trimethyl-2,6,10-dodecatrienyl)oxy]methyl]phosphinic acid

A stirred suspension of 86.6 mg (0.26 mmol) of Example 13 ester in 2 mL of water was treated with 0.5 mL of 1M KOH under argon at room temperature. The oil dissolved rapidly to give a cloudy solution. After 30 minutes, the mixture was extracted with ethyl acetate, the aqueous layer diluted with a second portion of ethyl acetate and acidified with 1M HCl. The second organic extract was washed with water and brine, dried (MgSO$_4$) and evaporated to provide 63.3 mg (81%) of title compound as a colorless oil which may be used in preparing compounds of the invention.

TLC Silica gel (8:1:1 CH$_2$Cl$_2$:acetic acid:CH$_3$OH) $R_f$=0.34.

EXAMPLE 17

(E,E)-[Hydroxy[[(3,7,11-trimethyl-2,6,10-dodecatrienyl)oxy]methyl]phosphinyl]formic acid, disodium salt To a stirred solution of 63.5 mg (0.19 mmol) of Example 16 compound in 1 mL of CH$_2$Cl$_2$ was added 72 μL (0.57 mmol) of chlorotrimethylsilane, 36 μL (0.38 mmol) of ethyl chloroformate and 80 mL (0.57 mmol) of triethyl amine. The solution was evaporated, the residue was dissolved in 2.5 mL of 1M NaOH and stirred at room temperature for 68 hours. The solution was lyophilized to provide title compound contaminated with the sodium salt of the Example 16 compound.

TLC Silica gel (7:2:1 n-C$_3$H$_7$OH:con NH :H$_2$O) $R_f$=0.42

EXAMPLES 18 TO 91

Following procedures of Examples 1 to 17, the following additional compounds may be prepared in accordance with the present invention. It will be appreciated that the compounds listed include all stereoisomers thereof.

$$CH_3-\underset{\underset{CH_3}{|}}{C}=\underset{H}{\overset{H}{C}}-\underset{\underset{H}{|}}{\overset{H}{C}}\underset{\underset{H}{|}}{\overset{H}{C}}-C=\underset{\underset{CH_3}{|}}{CH}-CH_2-Q^4-(CH_2)_p-X-(CH_2)_q-\underset{\underset{OR^2}{|}}{\overset{\overset{O}{\|}}{P}}-\overset{\overset{O}{\|}}{C}-OR^3$$

| Ex. No. | Q$^4$ | X | p | q | R$^3$ | R$^2$ |
|---|---|---|---|---|---|---|
| 18. | —CH$_2$—C(=CH—CH$_2$—)CH$_3$ | O | 2 | 0 | K | K |

-continued

| | | | | | | |
|---|---|---|---|---|---|---|
| 19. | bond | O | 0 | 1 | Na | Na |
| 20. | bond | O | 1 | 0 | Na | Na |
| 21. | -CH₂-C(CH₃)=CH-CH₂- | O | 1 | 1 | Na | Na |
| 22. | ( -CH₂-C(CH₃)=CH-CH₂- )₂ | O | 1 | 0 | K | K |
| 23. | -CH₂-C(CH₃)=CH-CH₂- | — | 2 | 0 | CH₃ | K |
| 24. | -CH₂-C(CH₃)=CH-CH₂- | — | 0 | 1 | Na | Na |
| 25. | -CH₂-C(CH₃)=CH-CH₂- | O | 1 | 1 | K | K |
| 26. | ( -CH₂-C(CH₃)=CH-CH₂- )₂ | — | 3 | 0 | —Mg— | |
| 27. | -CH₂-C(CH₃)=CH-CH₂- | O | 1 | 0 | —Mg— | |
| 28. | -CH₂-C(CH₃)=CH-CH₂- | — | 1 | 1 | Na | Na |
| 29. | -CH₂-C(CH₃)=CH-CH₂- | O | 2 | 1 | Na | Na |
| 30. | ( -CH₂-C(CH₃)=CH-CH₂- )₂ | O | 2 | 0 | K | K |
| 31. | -CH₂-C(CH₃)=CH-CH₂- | — | 2 | 0 | —Mg— | |
| 32. | bond | O | 2 | 0 | Na | Na |
| 33. | -CH₂-C(CH₃)=CH-CH₂- | — | 1 | 1 | K | K |

-continued

| | | | | | | | |
|---|---|---|---|---|---|---|---|
| 34. | | bond | O | 1 | 1 | Na | Na |

Structure:
$CH_3$-C(=CH-...)... with $R^7$, $R^8$, $R^6$ substituents, $(CH_2)_p$-X-$(CH_2)_q$-P(=O)(O$R^2$)-C(=O)-O$R^3$

| Ex. No. | $R^7$ | $R^6$ | $R^8$ | p | X | q | $R^2$ | $R^3$ |
|---|---|---|---|---|---|---|---|---|
| 35. | H | F | H | 1 | 0 | 0 | K | K |
| 36. | H | H | F | 0 | 0 | 1 | Na | Na |
| 37. | H | $CH_3$ | $CH_3$ | 1 | 0 | 0 | —Mg— | |
| 38. | $CH_3S$ | $CH_3$ | H | 1 | 0 | 1 | K | K |
| 39. | F | $CH_3$ | H | 2 | — | 0 | Na | Na |
| 40. | $CH_3$ | $CH_3$ | H | 1 | 0 | 0 | K | K |
| 41. | H | $CH_3$ | $CH_3$ | 2 | — | 0 | Na | Na |
| 42. | H | $CH_3$ | F | 1 | 0 | 0 | K | K |
| 43. | H | $CF_3$ | H | 1 | 0 | 0 | K | K |
| 44. | H | F | H | 0 | 0 | 1 | K | K |
| 45. | H | $CH_3$ | $(CH_3)_3Si$ | 1 | 0 | 0 | Na | Na |
| 46. | H | $CH_3$ | F | 1 | 0 | 0 | K | K |

Structure with $R^{10}$, $R^{11}$ substituents.

| Ex. No. | $R^{10}$ | $R^{11}$ | p | X | q | $R^2$ | $R^3$ |
|---|---|---|---|---|---|---|---|
| 47. | $C_2H_5$ | $CH_3$ | 1 | 0 | 0 | $CH_3$ | K |
| 48. | $CH_3$ | $C_2H_5$ | 1 | 0 | 0 | Na | Na |
| 49. | n-$C_3H_7$ | $CH_3$ | 0 | 0 | 1 | —Mg— | |
| 50. | $CH_3$ | n-$C_3H_7$ | 2 | — | 0 | K | K |
| 51. | $CH_3$ | n-$C_4H_9$ | 1 | 0 | 0 | K | $CH_3$ |
| 52. | t-$C_4H_9$ | $CH_3$ | 1 | 0 | 0 | K | K |
| 53. | —$(CH_2)_5$— | | 2 | 0 | 1 | K | K |
| 54. | H | H | 2 | — | 0 | Na | Na |
| 55. | F | F | 2 | — | 0 | —Mg— | |
| 56. | F | F | 1 | 0 | 0 | K | K |
| 57. | $CH_2F$ | $CH_3$ | 1 | 0 | 0 | Na | Na |
| 58. | —CH=$CH_2$ | H | 0 | 0 | 1 | K | K |

Structure with $R^{11}$, $R^6$, $R^{6'}$ substituents.

| Ex. No. | $R^{11}$ | $R^6$ | $R^{6'}$ | p | X | q | $R^2$ | $R^3$ |
|---|---|---|---|---|---|---|---|---|
| 59. | $C_2H_5$ | $C_2H_5$ | $CH_3$ | 1 | 0 | 0 | K | K |
| 60. | $CH_3$ | $CH_3$ | $C_2H_5$ | 1 | 0 | 0 | Na | Na |
| 61. | $CH_3$ | $C_2H_5$ | $C_2H_5$ | 2 | — | 0 | Mg | |
| 62. | $C_2H_5$ | $C_2H_5$ | $C_2H_5$ | 0 | 0 | 1 | $CH_3$ | K |
| 63. | $CH_3$ | $C_2H_5$ | $CH_3$ | 1 | — | 1 | K | K |
| 64. | $CH_3$ | H | $CH_3$ | 1 | 0 | 0 | Na | Na |
| 65. | $CH_3$ | $CH_3$ | H | 2 | 0 | 0 | K | K |
| 66. | H | H | H | 1 | 0 | 0 | K | K |

Ex. No.

67.

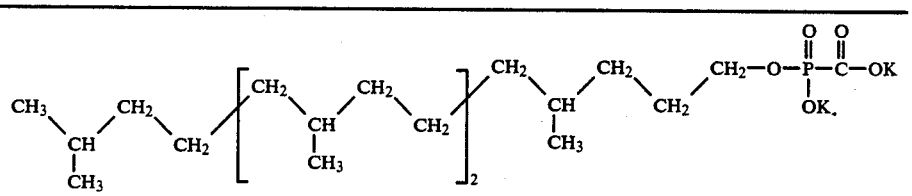

-continued
68. 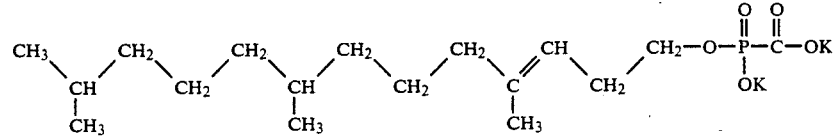
69. 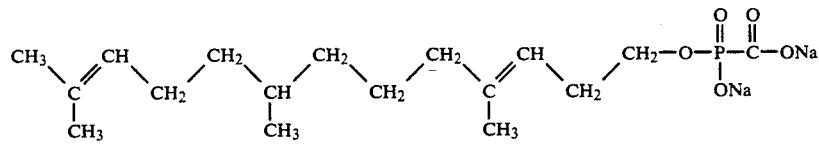
70. 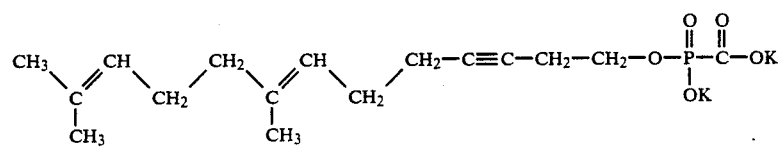
71. 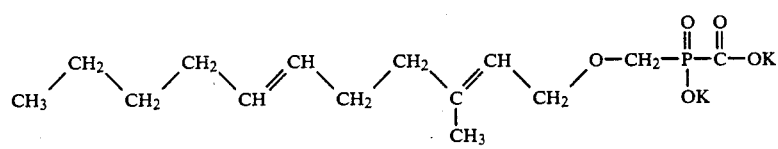
72. 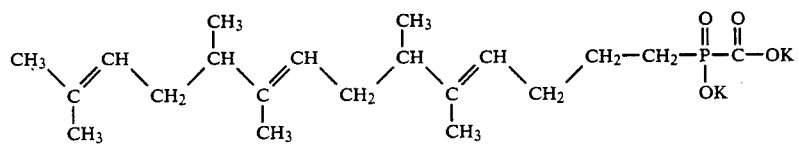
73. 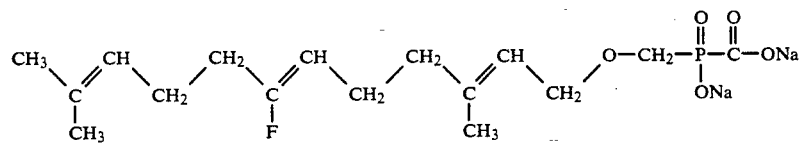
74. 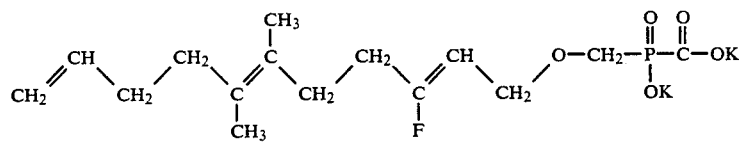
75. 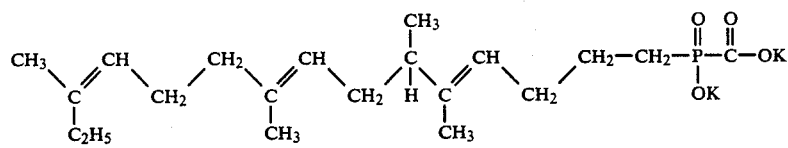
76. 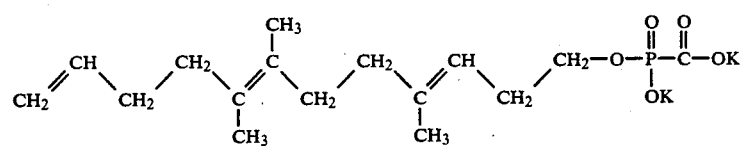
77. 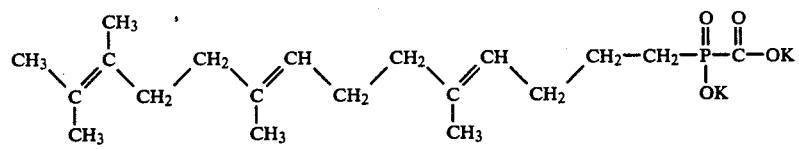
78. 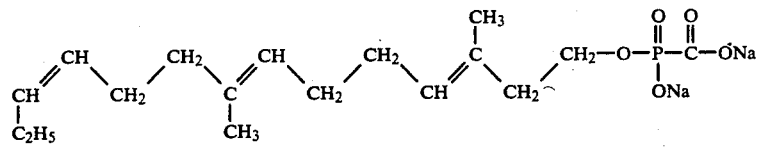

-continued
79. 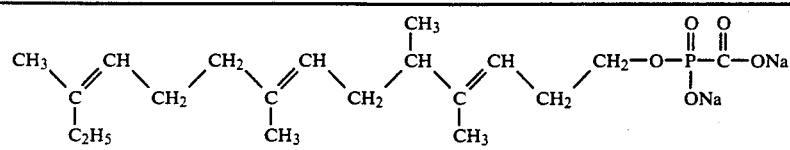
80. 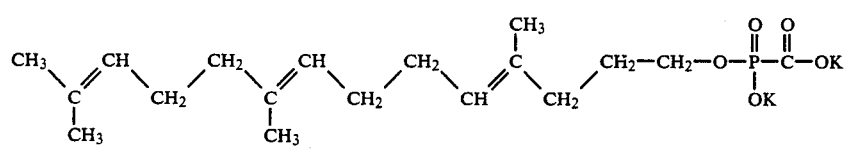
81. 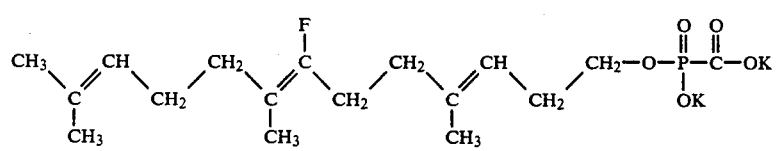
82. 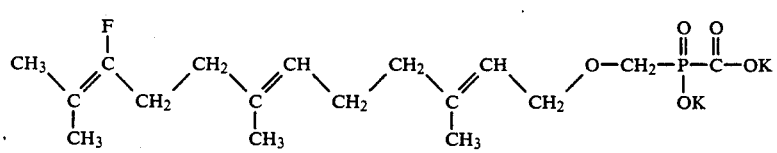
83. 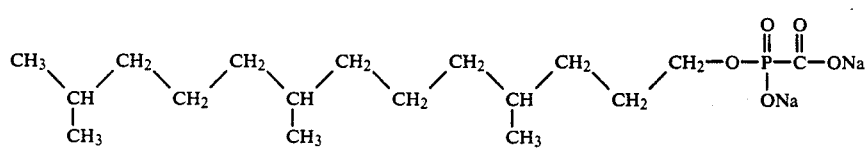
84. 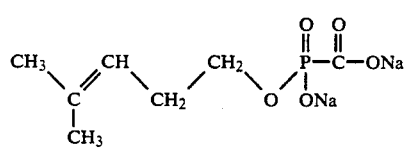
85. 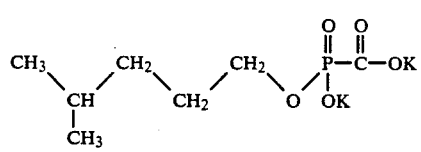
86. 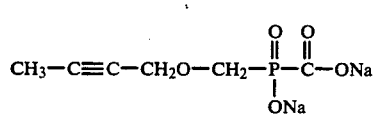
87. 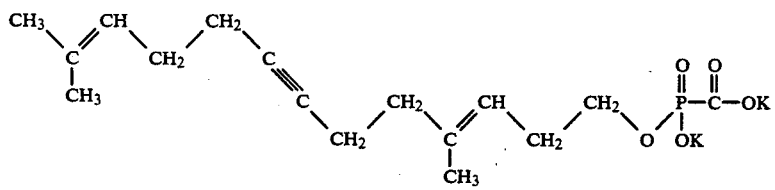
88. 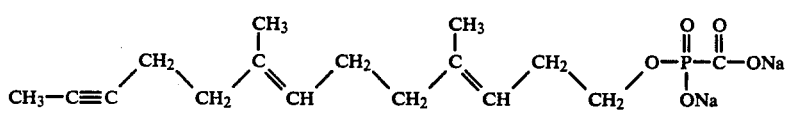
89. 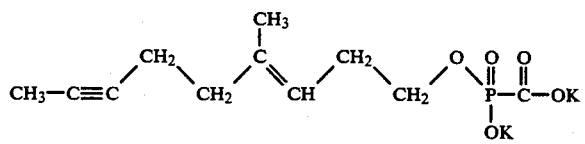

-continued

90. 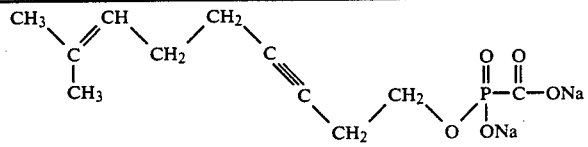

91. 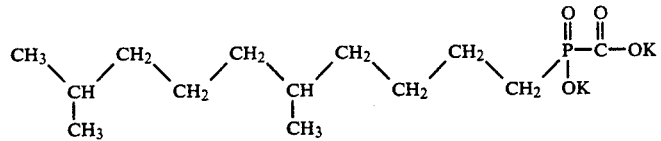

What is claimed is:

1. A process for preparing a compound having the formula

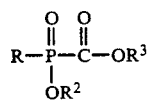

wherein $R^2$ is an alkali metal or lower alkyl; $R^3$ is an alkali metal or lower alkyl; R is $R^1—(CH_2)_n—$ or $R^1—(CH_2)_mOCH_2—$, wherein n is an integer from 1 to 4 and m is an integer from 0 to 3; and $R^1$ is $R^5—Q^1—Q^2—Q^3—$ wherein $Q^1$, $Q^2$ and $Q^3$ are independently:

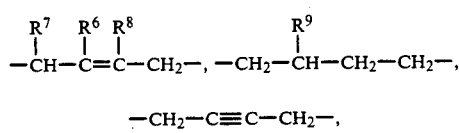

or a bond with the stipulation that if $Q^1$ is a bond, then $Q^2$ and $Q^3$ must be bonds, and if $Q^2$ is a bond, then $Q^3$ is a bond; if any of $Q^1$, $Q^2$ and $Q^3$ is

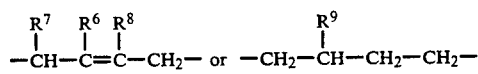

then $R^6$ is H, lower alkyl, fluoro or fluoroalkyl; $R^7$ is H, fluoro, lower alkyl or alkylthio; $R^8$ is H, fluoro, trimethylsilyl or lower alkyl; $R^9$ is H, or lower alkyl;

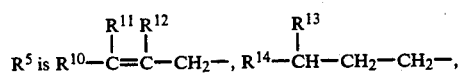

$R^{16}—C\equiv C—CH_2—$ (wherein $R^{16}$ is lower alkyl or H), or $CH_3(CH_2)_p—$ where p is 2 to 7; $R^{10}$ and $R^{11}$ are independently hydrogen, lower alkyl, fluoro, lower alkenyl or fluoroalkyl or $R^{10}$ and $R^{11}$ can be taken together to form $(CH_2)_s$, where s is 2 to 7; $R^{12}$ is hydrogen, lower alkyl, fluoro or lower alkenyl; $R^{13}$ and $R^{14}$ are independently lower alkyl; with the proviso that if all of $Q^1$, $Q^2$ and $Q^3$ are bonds, then $R^{10}$ and $R^{11}$ cannot both be H, and $R^5$ cannot be $CH_3(CH_2)_p—$, with $p \leq 4$, including all stereoisomers thereof, which comprises treating a compound of the structure R-Metal where R is as defined above, with a phosphite of the structure $ClP(OR^2)_2$ wherein $R^2$ is lower alkyl, to form a phosphonite of the structure $R—P(OR^2)_2$ and treating the phosphonite with an alkylating agent of the structure $ClCO_2R^3$ to form the phosphinylformate diester of the structure

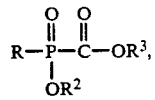

and optionally, if desired, treating the so-formed phosphinylformate diester with a dealkylating agent and one molar equivalent of alkali metal base to form the metal salt of the structure

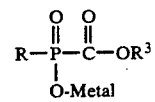

and optionally treating said metal salt with a strong acid to form the acid of the structure

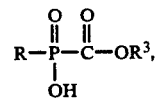

or optionally, if desired, treating the so-formed phosphinylfomrate diester with a dealkylating agent and/or excess alkali metal base to form the dimetal salt of the structure

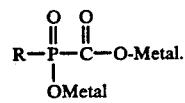

2. The process as defined in claim 1 wherein R is $R^1—(CH)_{2n}—$.

3. The process as defined in claim 1 wherein R is $R^1—(CH_2)_m—O—CH_2—$.

4. The process as defined in claim 1 wherein $R^1$ is

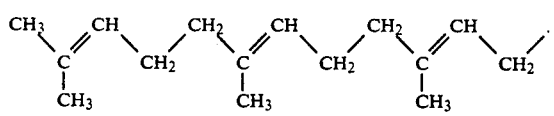
5. The process as defined in claim 1 wherein R is $R^1\text{-}(CH_2)_n\text{-}$ and n is 1, 2 or 3.
6. The process as defined in claim 1 wherein R is $R^1\text{-}(CH_2)_m OCH_2\text{-}$ wherein m is 1.
7. The process as defined in claim 1 wherein $R^2$ is a metal ion and/or $R^3$ is a metal ion.
* * * * *